US009472217B2

(12) United States Patent
Heidmann

(10) Patent No.: US 9,472,217 B2
(45) Date of Patent: *Oct. 18, 2016

(54) MAGNETIC WRITE HEAD CHARACTERIZATION WITH NANO-METER RESOLUTION USING NITROGEN VACANCY COLOR CENTERS

(71) Applicant: Infinitum Solutions, Inc., Santa Clara, CA (US)

(72) Inventor: Juergen Heidmann, Salinas, CA (US)

(73) Assignee: Infinitum Solutions, Inc., Santa Clara, CA (US)

( * ) Notice: Subject to any disclaimer, the term of this patent is extended or adjusted under 35 U.S.C. 154(b) by 175 days.

This patent is subject to a terminal disclaimer.

(21) Appl. No.: 14/532,992

(22) Filed: Nov. 4, 2014

(65) Prior Publication Data

US 2015/0235661 A1 Aug. 20, 2015
US 2016/0071532 A9 Mar. 10, 2016

Related U.S. Application Data

(63) Continuation-in-part of application No. 14/184,610, filed on Feb. 19, 2014, now Pat. No. 8,885,301.

(60) Provisional application No. 61/950,596, filed on Mar. 10, 2014.

(51) Int. Cl.
*G11B 5/02* (2006.01)
*G11B 5/33* (2006.01)
(Continued)

(52) U.S. Cl.
CPC .............. *G11B 5/455* (2013.01); *G01N 24/08* (2013.01); *G11B 2005/0021* (2013.01)

(58) Field of Classification Search
CPC ................... G11B 5/6088; G11B 2005/0021; G11B 2005/0005; G11B 5/314; G11B 25/043; G11B 33/08; G11B 27/36; G11B 5/012; G11B 5/40; G11B 5/11; B08Y 25/00; G01D 5/38; G01R 33/26
USPC ........... 360/59, 323, 324.12, 324.22, 114.01, 360/97.12, 31; 369/13.33, 130.02, 112.23; 356/395; 324/304
See application file for complete search history.

(56) References Cited

U.S. PATENT DOCUMENTS 5,770,856 A 6/1998 Fillard et al.
6,259,104 B1 7/2001 Baer
(Continued)

FOREIGN PATENT DOCUMENTS

WO WO 2014/051886 A1 4/2014

OTHER PUBLICATIONS

Choy, J. et al. (May 20, 2011). Enhanced Single Photon Emission from a Diamond-Silver Aperture, arXIV:1105.4096v1 [*quant-ph*] p. 1-16.
(Continued)

*Primary Examiner* — Nabil Hindi
(74) *Attorney, Agent, or Firm* — Silicon Valley Patent Group LLP

(57) ABSTRACT

A crystal film with one or more nitrogen vacancy centers is placed in close proximity to a recording head. A magnetic field or heat produced by the recording head as well as excitation illumination and an excitation field is applied to the crystal film. The magnetic field produced by the recording head, the heat produced by a thermal device on the recording head, and/or the excitation field may be varied. A confocal microscope or wide-field microscope optically detects a decrease in a spin dependent photoluminescence in response to the magnetic field or heat, excitation field and excitation illumination caused by electron spin resonance (ESR) of the at least one nitrogen vacancy center to measure Optically Detected Spin Resonance (ODMR). A characteristic of the recording head is determined using the ODMR.

85 Claims, 21 Drawing Sheets

(51) Int. Cl.
  *G11B 5/455* (2006.01)
  *G01N 24/08* (2006.01)
  *G11B 5/00* (2006.01)

(56) References Cited

U.S. PATENT DOCUMENTS

| | | | |
|---|---|---|---|
| 6,389,210 | B1 | 5/2002 | Mukasa et al. |
| 6,891,151 | B2 | 5/2005 | Shimada et al. |
| 7,305,869 | B1 | 12/2007 | Berman et al. |
| 7,861,316 | B2 | 12/2010 | van der Weide et al. |
| 8,193,808 | B2 | 6/2012 | Fu et al. |
| 8,415,640 | B2 | 4/2013 | Babinec et al. |
| 8,455,278 | B2 | 6/2013 | Linares et al. |
| 8,547,090 | B2 | 10/2013 | Lukin et al. |
| 8,885,301 | B1 | 11/2014 | Heidmann |
| 2010/0308813 | A1 | 12/2010 | Lukin et al. |
| 2012/0019242 | A1 | 1/2012 | Hollenberg et al. |
| 2013/0032734 | A1 | 2/2013 | Santori et al. |
| 2014/0166904 | A1 | 6/2014 | Walsworth et al. |
| 2015/0235661 | A1 | 8/2015 | Heidmann |
| 2015/0253355 | A1 | 9/2015 | Grinolds et al. |

OTHER PUBLICATIONS

Doherty, M. et al. (Oct. 28, 2013). "The temperature shifts of the resonances of the NV-center in diamond," arXiv:1310.7303v1 [cond-mat.mtrl-sci] p. 1-6.
Epstein, R. et al. (2005). "Anisotropic interactions of a single spin and dark-spin spectroscopy in diamond," Center for Spintronics and Quantum Computation, University of California, Santa Barbara, CA, p. 1-17.
Fuchs, G. et al. (Jun. 11, 2008). "Excited-state spectroscopy using single-spin manipulation in diamond," arXiv:0806.1939v1 [quant-ph] p. 1-15.
Greffet, J.-J. et al. (Jul. 3, 2011). "Diamond particles as nanoantennas for nitrogen-vacancy color centers," arXiv:1107.0502v1 [physics.optics] p. 1-4.
Grinolds, M. et al. (Sep. 2, 2012). "Nanoscale magnetic imaging of a single electron spin under ambient conditions," arXiv:1209.0203v1 [cond-mat.mes-hall] p. 1-12.
Gruber, A. et al. (1997). "Scanning Confocal Optical Microscopy and Magnetic Resonance on Single Defect Centers," *Science* 276: 2012.
Han, K. et al. (Jul. 22, 2010). "Metastable Dark States Enable Ground State Depletion Microscopy of Nitrogen Vacancy Centers in Diamond with Diffraction-Unlimited Resolution," *Nano Lett* 10: 3199-3203.
Hausmann, B. et al. (Apr. 5, 2011). "Single-color centers implanted in diamond nanostructures," *New Journal of Physics* 13(045004):1-11.
Hong, S. et al. (Feb. 8, 2012). "Coherent, mechanical control of a single electronic spin," arXiv:1202.1823v1 [cond-mat.mes-hall] p. 1-6.
Horowitz, V. et al. (Jun. 7, 2012). "Electron spin resonance of nitrogen-vacancy centers in optically trapped nanodiamonds," arXIV:1206.1573v1 [cond-mat.mtrl-sci] p. 1-29.
Kucsko, G. et al. (Apr. 3, 2013). "Nanometer scale quantum thermometry in a living cell," arXIV:1304.1068v1 [quant-ph] p. 1-22.
Lai, N. et al. (Sep. 8, 2009). "Influence of a static magnetic field on the photoluminescence of an ensemble of Nitrogen-Vacancy color centers in a diamond single-crystal," arXiv:0908.1327v2 [cond-mat.mtrl-sci] p. 1-4.
Laraoui, A. et al. (May 7, 2013). "High-Resolution Correlation Spectroscopy of 13C Spins Near a Nitrogen-Vacancy Center in Diamond," arXiv:1305.1536v1 [cond-mat.mes-hall] p. 1-22.
Lesik, M. et al. (Jan. 13, 2014). "Perfect preferential orientation of nitrogen-vacancy defects in a synthetic diamond sample," arXiv:1401.2795v1 [cond-mat.mtrl-sci] p. 1-6.

Maclaurin, D. et al. (Jul. 23, 2012). "Nanoscale magnetometry through quantum control of nitrogen-vacancy centres in rotationally diffusing nanodiamonds," arXIV:1207.5276v1 [quant-ph] p. 1-9.
Malentinsky, P. et al. (Aug. 22, 2011). "A robust, scanning quantum system for nanoscale sensing and imaging," arXiv:1108.4437v1 [cond-mat.mes-hall] p. 1-11.
Mamin, H. et al. (Feb. 1, 2013). "Nanoscale Nuclear Magnetic Resonance with a Nitrogen-Vacancy Spin Sensor," *Science* 339: 557-560.
Mamin, H. et al. (Sep. 14, 2012). "Detecting External Electron Spins Using Nitrogen-Vacancy Centers," IBM Research Division, Almaden Research Center, San Jose, CA, p. 1-25.
Meijer, J. et al. (May 1, 2008). "Towards the implanting of ions and positioning of nanoparticles with nm spatial resolution," *Appl. Phys. A* 91:567-571.
Michl, J. et al. (Jan. 16, 2014). "Perfect alignment and preferential orientation of nitrogen-vacancy centers during CVD growth on (111) surfaces," arXiv:1401.4106v2 [cond-mat.mes-hall] p. 1-6.
Neumann, P. et al. (Apr. 2, 2013). "High precision nano scale temperature sensing using single defects in diamond,"arXIV:1304.0688v1 [quant-ph] p. 1-6.
Pham, L. et al. (Apr. 28, 2011). "Magnetic field imaging with nitrogen-vacancy ensembles," *New Journal of Physics* 13(045021):1-13.
Rittweger, E. et al. (Feb. 22, 2009). "STED microscopy reveals crystal colour centres with nanometric resolution," *Nature Photonics* DOI:10.1038/NPHOTON.2009.2:1-4.
Rondin, L. et al. (Apr. 13, 2012). "Nanoscale magnetic field mapping with a single spin scanning probe magnetometer," arXiv:1108.4438v3 [cond-mat.mes-hall] p. 1-10.
Schirhagl, R. et al. (Nov. 12, 2013). "Nitrogen-Vacancy Centers in Diamond: Nanoscale Sensors for Physics and Biology," *Annu. Rev. Phys. Chem.* 2014(65):83-105.
Taylor, J. et al. (May 9, 2008). "High-sensitivity diamond magnetometer with nanoscale resolution," arXiv:0805.1367v1 [cond-mat.mes-hall] p. 1-29.
Tetienne, J-P. (Oct. 19, 2012). "Magnetic-field dependent photodynamics of single NV defects in diamond: An application to qualitative all-optical magnetic imaging," *New Journal of Physics* 14(103033):1-15.
Toyli, D. et al. (Jul. 16, 2012). "Measurement and control of single nitrogen-vacancy center spins above 600K," arXIV:1201.4420v2 [cond-mat.mes-hall] p. 1-22.
Toyli, D. et al. (Jul. 23, 2010). "Chip-Scale Nanofabrication of Single Spins and Spin Arrays in Diamond," *Nano Lett* 10:3168-3172.
Toyli, D. et al. (Mar. 27, 2013). "Fluorescence thermometry enhanced by the quantum coherence of single spins in diamond," arXIV:1303.6730v2 [cond-mat.mes-hall] p. 1-15.
Wrachstrup et al. (2009). "Single Spins in Diamond-Probes for Nanoscience," Molecular Imaging, Cornell University, Ithaca, p. 1-27.
Notice of Allowance mailed on Jul. 10, 2014 for U.S. Appl. No. 14/184,610, filed Feb. 19, 2014 by Infinitum Solutions, Inc., 11 pages.
Challener et al. "Near-field optics for heat-assisted magnetic recording (experiment, theory, and modeling)," *Modelling and Numerical Simulations II*, Modern Aspects of Electrochemistry 44:53-110, 2009.
Chen et al. "Sub-diffraction optical manipulation of the chargestate of nitrogen vacancy center in diamond", ArXiv e-prints, 21 pages, 2014.
Chernyshov et al. "Measurement of Magnetic Properties Relevant to Heat-Assisted-Magnetic-Recording", *IEEE Transactions on Magnetics* 49(7):3572-3575, 2013.
Chmyrov et al. "Nanoscopy with more than 100,000 'doughnuts'" *Nature Methods* 10(8):737-743, 2013.
Han et al. "Three-Dimensional Stimulated Emission Depletion Microscopy of Nitrogen-Vacancy Centers in Diamond Using Continuous-Wave Light", *Nano Lett* 9(9):3323-3329, 2009.
Hao et al. "Effects of polarization on the de-excitation dark focal spot in STED microscopy", *Journal of Optics* 12(11):115707-1-8, 2010.

(56) References Cited

OTHER PUBLICATIONS

Moneron et al. "Two-photon excitation STED microscopy," *Opt Express* 17(17):14567-14573, 2009.
Rittweger et al. "Far-field fluorescence nanoscopy of diamond color centers by ground state depletion," *EPL (Europhysics Letters)* 86(1):14001, 2009.
Rittweger, E. et al. "STED microscopy reveals crystal colour centres with nanometric resolution," *Nature Photonics* DOI:10.1038/NPHOTON.2009.2:1-4, 2009.
Rottmayer et al. "Heat-Assisted Magnetic Recording," *IEEE Trans Magnetics* 42(10):2417-2421, 2006.
Schrof et al. "STED nanoscopy with mass-produced laser diodes," *Optics Express* 19(9): 8066-8072, 2011.
Seigler et al. "Integrated Heat Assisted Magnetic Recording Head: Design and Recording Demonstration," *IEEE Trans Magnetics* 44(1):119-124, 2008.
Vicidomini et al. "STED Nanoscopy with Time-Gated Detection: Theoretical and Experimental Aspects," *PLOS One* 8(1):e54421:1-12, 2013.
Wang et al. "Time-gated STED nanoscopy," located at http://www.paper.edu.cn, p. 1-8, 2013.
Willig et al. "STED microscopy with continuous wave beams," *Nat Meth* 4(11):915-918, 2007.
Grinolds. (2014). "Nanoscale Magnetic Resonance Imaging and Magnetic Sensing Using Atomic Defects in Diamond," PhD thesis. Harvard University: Cambridge, Massachusetts, 152 pages.
Lai et al. (2013). "Quenching nitrogen-vacancy center photoluminescence with an infrared pulsed laser," New J. Phys.15 033030 <http://iopscience.iop.org/1367-2630/15/3/033030>.
Le Sage et al. (2012). "Efficient Photon Detection from Color Centers in a Diamond Optical Waveguide," *Physical Review B* 85:121202-1-4.
Maletinsky. (2012). "A Robust Scanning Diamond Sensor for Nanoscale Imaging with Single Nitrogen-Vacancy Centres," *Nature Nanotechnology* vol. 7: 320-324.
Taylor et al. (2008). "High-Sensitivity Diamond Magnetometer with Nanoscale Resolution," *Nature Physics* vol. 4:810-816.
U.S. Appl. No. 14/542,410, filed Nov. 14, 2014 by Infinitum Solutions, Inc., 53 pages.

Write Field Distribution
(Homogenous)

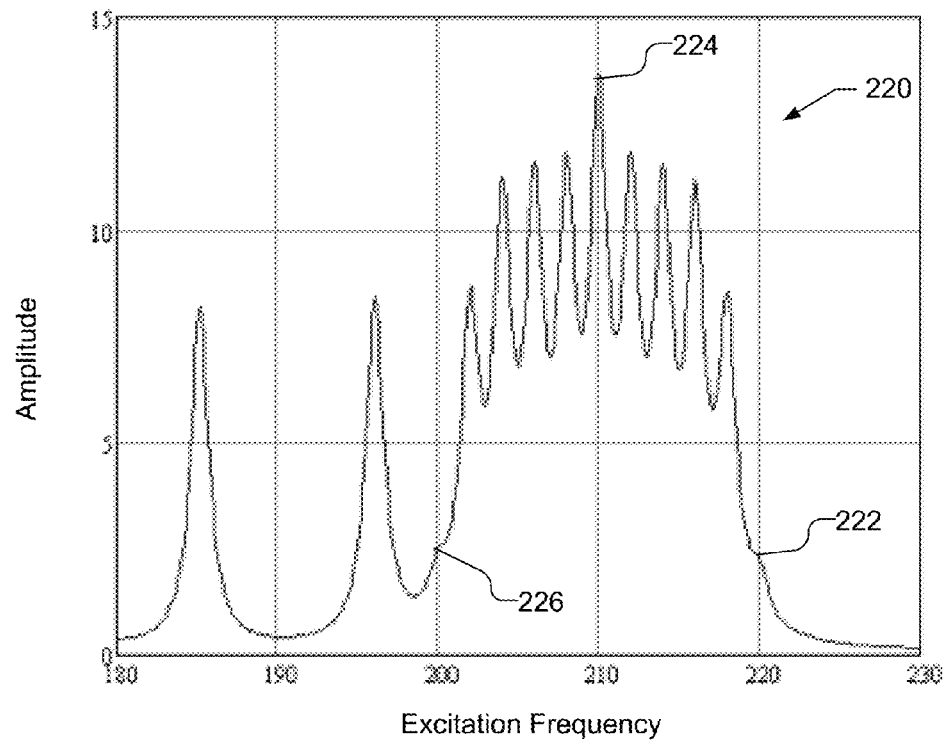
Fig. 18
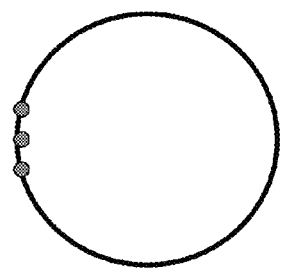 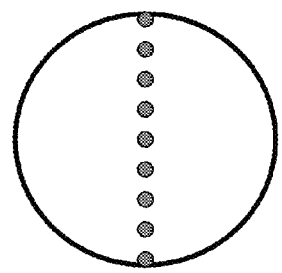 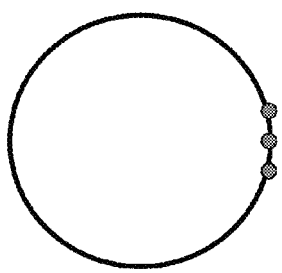
Fig. 19A   Fig. 19B   Fig. 19C

MAGNETIC WRITE HEAD CHARACTERIZATION WITH NANO-METER RESOLUTION USING NITROGEN VACANCY COLOR CENTERS

CROSS REFERENCE TO RELATED APPLICATIONS

This application is a continuation-in-part of U.S. application Ser. No. 14/184,610, filed Feb. 19, 2014, and claims priority under 35 USC 119 to U.S. Provisional Application No. 61/950,596, filed Mar. 10, 2014, both of which are incorporated by reference herein in their entireties.

BACKGROUND

As critical dimensions in magnetic data storage systems, e.g. hard disk drives, are continuing to shrink to a few tens of nanometers, the development of characterization techniques that may be used in manufacturing or research and development has become increasingly demanding. For example, optical and magneto-optical metrology methods do not provide the spatial resolution required to determine properties of the write-field emanating from the write pole on the nanometer length scale. Magnetic Force Microscopy, on the other hand, has high spatial resolution but does not provide quantitative information about the magnetic field strength. In addition, current magnetic recording heads include other features that are on the nanometer length scale that are desirable to characterize, but that cannot be adequately measured using conventional metrology systems. By way of example, some magnetic recording heads include features such as optical nano-apertures for heat assisted magnetic recording (HAMR), for which characterization of the optical power in the near-field of these nano-apertures is desired. Accordingly, improved metrology methods for characterizing, e.g., magnetic recording heads is desired.

SUMMARY

A crystal film with one or more nitrogen vacancy centers is placed in close proximity to a recording head. A magnetic field or heat produced by the recording head as well as excitation illumination and an excitation field is applied to the crystal film. The magnetic field produced by the recording head, the heat produced by a thermal device on the recording head, and/or the excitation field may be varied. A confocal microscope or wide-field microscope optically detects a decrease in a spin dependent photoluminescence in response to the magnetic field or heat, excitation field and excitation illumination caused by electron spin resonance (ESR) of the at least one nitrogen vacancy center to measure Optically Detected Spin Resonance (ODMR). A characteristic of the recording head is determined using the ODMR.

In one implementation, a method includes providing a bias signal to a recording head that includes a write pole to produce a magnetic field from the recording head, wherein a crystal film with nitrogen vacancy centers is positioned in the magnetic field; providing an excitation field to the crystal film; producing excitation illumination that is incident on the crystal film; measuring Optically Detected Spin Resonance (ODMR) by detecting a decrease in a spin dependent photoluminescence in response to the magnetic field, the excitation field and the excitation illumination caused by electron spin resonance (ESR) of the nitrogen vacancy centers; and determining a characteristic of the recording head using the ODMR.

In one implementation, an apparatus includes a biasing source configured to provide a bias signal; a probe card coupled to the biasing source and configured to be connected to a recording head that includes a write pole to provide the bias signal to the recording head that causes the recording head to produce a magnetic field; a light source that produces excitation illumination that is incident on a crystal film with nitrogen vacancy centers that is in the magnetic field produced by the recording head; a radio frequency antenna that provides an excitation field to the crystal film; a microscope configured to detect photoluminescence produced by the nitrogen vacancies in response to the excitation illumination; and a processor coupled to the microscope and configured to measure Optically Detected Spin Resonance (ODMR) by detecting a decrease in a spin dependent photoluminescence in response to the magnetic field, the excitation field, and the excitation illumination caused by electron spin resonance (ESR) of the nitrogen vacancy centers, and determine a characteristic of the recording head using the ODMR.

In one implementation, a method includes providing a bias signal to a device that includes a thermal device that is controlled by the bias signal to produce heat, wherein a crystal film with nitrogen vacancy centers is positioned to be heated by the thermal device; providing an excitation field to the crystal film; producing excitation illumination that is incident on the crystal film; measuring Optically Detected Spin Resonance (ODMR) by detecting a decrease in a spin dependent photoluminescence in response to the heat, the excitation field and the excitation illumination caused by electron spin resonance (ESR) of the nitrogen vacancy centers; and determining a characteristic of the device using the ODMR.

In one implementation, an apparatus includes a biasing source configured to provide bias signals; a probe card coupled to the biasing source and configured to be connected to a device that includes a thermal device, the probe card provides a bias signal to the device that causes the thermal device to heat a crystal film, the crystal film includes nitrogen vacancy centers; a light source that produces excitation illumination that is incident on the crystal film; a radio frequency antenna that provides an excitation field to the crystal film; a microscope configured to detect photoluminescence produced by the nitrogen vacancies in response to the excitation illumination; and a processor coupled to the microscope and configured to measure Optically Detected Spin Resonance (ODMR) by detecting a decrease in a spin dependent photoluminescence in response to the heat, the excitation field, and the excitation illumination caused by electron spin resonance (ESR) of the nitrogen vacancy centers; and determine a characteristic of the device using the ODMR.

In one implementation, a method includes providing a bias signal to a recording head that includes a write pole to produce a magnetic field from the recording head; scanning a probe having a probe tip comprising a crystal particle with at least one nitrogen vacancy center through the magnetic field produced by the recording head; providing an excitation field to the crystal particle; producing excitation illumination that is incident on the crystal particle; measuring Optically Detected Spin Resonance (ODMR) by detecting a decrease in a spin dependent photoluminescence in response to the excitation illumination caused by electron spin resonance (ESR) of the at least one nitrogen vacancy center; and determining a characteristic of the recording head using the ODMR.

In one implementation, an apparatus includes a biasing source configured to provide a bias signal; a probe card coupled to the biasing source and configured to be connected to a recording head that includes a write pole to provide the bias signal to the recording head that causes the recording head to produce a magnetic field; a probe having a probe tip comprising a crystal particle with at least one nitrogen vacancy center, the probe configured to be scanned through the magnetic field produced by the recording head; a light source that produces excitation illumination that is incident on the crystal particle; a radio frequency antenna that provides an excitation field to the crystal particle; a microscope configured to detect photoluminescence produced by the at least one nitrogen vacancy in the crystal particle; a processor coupled to the microscope and configured to measure Optically Detected Spin Resonance (ODMR) by detecting a decrease in a spin dependent photoluminescence in response to the excitation illumination caused by electron spin resonance (ESR) of the at least one nitrogen vacancy center; and determine a characteristic of the recording head using the ODMR.

BRIEF DESCRIPTION OF THE DRAWINGS

FIG. 18 illustrates a magnified view of a resonance peak from FIG. 17.

FIGS. 19A, 19B, and 19C illustrate nitrogen vacancy centers with the same resonance conditions when measuring ODMR in an in-homogenous write field distribution.

DETAILED DESCRIPTION

Figure 1:
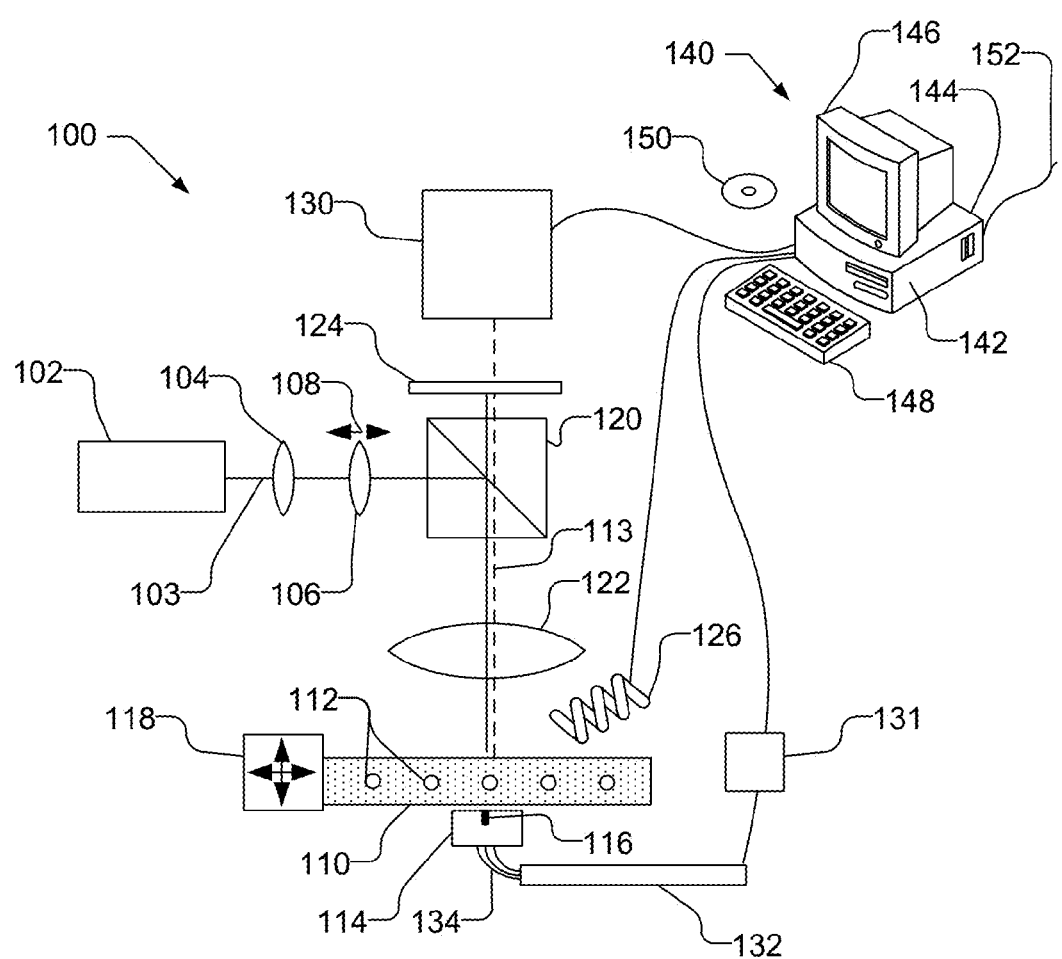
FIG. 1 illustrates an optical metrology device capable of characterizing magnetic recording heads using photoluminescence produced by a substitutional impurity in a crystal.

FIG. 1 illustrates an optical metrology device 100 capable of characterizing magnetic recording heads using photoluminescence produced by a substitutional impurity 112 in a crystal 110. For example, one or more nitrogen vacancy centers (NV centers) in a diamond crystal may be used. An NV center is a naturally occurring or technically created impurity in a diamond crystal where a Nitrogen atom replaces a Carbon atom creating a vacancy next to the Nitrogen atom. The diamond crystal, by way of example, may have a (111) crystal orientation, but other crystalline orientations are possible. If desired, other substitutional impurities in crystals may be used, such as the Silicon-vacancy center in diamond (SiV-), but for the sake of simplicity, the present disclosure will refer to nitrogen NV centers in diamond. The crystal may be, e.g., a crystal film that contains a plurality of NV centers or a crystal particle that contains a single (or a few) NV centers. If desired, a film may be produced that contains a plurality of crystal particles in a suspension forming a film on, e.g. a glass substrate, each crystal particle having one or more NV centers.

The NV centers, which are basically artificial atoms with distinct quantum energy levels, show unique extrinsic and intrinsic optical spin dynamics including stable photoluminescence (PL) based on radiating transitions between optically excited energy levels of their charged quantum states. The PL is temperature as well as magnetic field dependent. Further, Electron Spin Resonance (ESR) is excited in the NV center electronic spin system by an external radio frequency (RF)-field with frequencies resonant with the transitions between the energy sub-levels. At resonance, the PL intensity is measurably reduced. Moreover, the ESR is linearly dependent on an applied magnetic field and, thus, one or more NV centers may be used as a magnetic field sensor with nanometer resolution using optically detected ESR (sometimes referred to herein as ODMR (Optically Detected Magnetic Resonance) (ESR is paramagnetic resonance that falls into this category)). The ESR is also temperature dependent, so that for a fixed applied magnetic field, the shift in ESR is a measure of temperature. For both magnetic field and temperature measurements, the spatial resolution is determined fundamentally by the size of a single NV center which is on the Ångström length scale. Accordingly, the optical metrology device 100 may optically detect the PL of one or more NV centers 112 in a crystal 110, e.g. using photon counting by employing a photo detector or by using a camera with high sensitivity, to measure a variety of characteristics of a recording head that has features with a nanometer length scale.

The optical metrology device 100 may be, e.g., a microscope such as a confocal microscope or a wide-field microscope. For example, a confocal microscope may include a light source 102 that produces excitation illumination 103 that is incident on the crystal 110 with the substitutional impurities 112. The use of a confocal detection system enables selection of PL coming from only a small volume of the crystal 110, e.g., 1 µm³, that is associated with the spot on the surface of the crystal 110 produced by the excitation illumination change. The light source 102 may be, e.g., a laser, LED, etc., that excites the NV center with a continuous (CW) or pulsed excitation illumination, with one or more wavelengths in a range of 460 nm to 580 nm, and which may be, e.g., 532 nm. With pulsed excitation illumination, the pulse width may be, e.g., approximately 800 ps with a 4-MHz repetition rate. The light source 102 may have a power density of, e.g., 40 kW/cm², to polarize the NV center by pumping it between the ground and the excited levels. The light from the light source 102 may be provided to a collimator consisting of lenses 104 and 106 either directly or by way of an intervening optical element, e.g., fiber optics or a light pipe. The collimator 104, 106 expands and collimates the light, which is focused by lens 122, which is also used to collect the PL emanating from the NV centers. In an embodiment in which the device is a confocal microscope, the lens 106 (and/or other appropriate lens(es)) may be moved back and forth, as illustrated by arrow 108 and/or a 2-dimensional steering-mirror system could be used to move the excitation illumination 103 relative to the back-aperture plane of the objective lens 122 scanning the focused beam 103 in the sample plane. Additionally, appropriate apertures may be used in an embodiment in which the microscope is a confocal microscope. Moreover, if desired, additional light sources may be used along with light source 102.

A beam splitter 120 receives the excitation illumination from the light source 102 and provides at least a portion of the excitation illumination to the objective lens 122. The excitation illumination is focused on the surface of the crystal 110 by the objective lens 122, which may have a high numerical aperture (NA=0.95) or an oil-immersion lens with an NA of, e.g. 1.3. The objective lens 122 may focus the excitation illumination on the crystal 110 at a normal angle of incidence. It should be understood, however, that an oblique angle of incidence of the excitation illumination may be used if desired. The objective lens 122 focuses the light onto the crystal 110 with one or more NV centers 112. The crystal 110 and NV centers 112 are positioned to be in a magnetic field produced by the recording head 114. The recording head 114 may be a magnetic recording head, such as that used in hard disk drives, and may be in any desired form factor including bar, slider, HGA (head gimbal assembly), and HSA (head stack assembly). Moreover, the recording head 114 may be a Heat Assisted Magnetic Recording (HAMR) write head or other type of magnetic recording head. The crystal 110 may be placed near or in contact with the recording head 114, or if desired, deposited on the recording head 114. Moreover, if desired, an intervening layer may be located between the crystal 110 and the recording head 114, such as a layer of a magnetic recording medium or a layer of material with low thermal conductivity that may be heated by a thermal device on a HAMR write head, or a reflecting layer. The NV centers 112 in the crystal 110 may have a relatively low density such that the distance between adjacent NV centers 112 is greater than a width of the write pole 116 to be measured in the recording head 114. Alternatively, a single NV center 112 may be used in the crystal 110. In such an embodiment, relative movement between the recording head 114 and the crystal 110 may be produced, e.g., as illustrated by actuator 118. Alternatively, the NV centers 112 in the crystal 110 may have a relatively high density such that the distance between adjacent NV centers 112 is similar to or less than the width of the write pole 116 to be measured in the recording head 114. With a relatively high NV center density, relative movement between the crystal 110 and the recording head 114 may not be necessary. Moreover, in some embodiments, movement between the crystal 110 and the recording head 114 may not be possible, for example, if the crystal 110 is applied directly to the recording head 114, e.g., during the manufacturing process. The optical metrology device 100, however, may include additional optic elements to move the excitation illumination over the crystal 110, e.g., in one or two dimensions. In another embodiment, no relative motion is employed, e.g., between the excitation illumination and the crystal or between the crystal and the write pole, but rather the integral ODMR signal is collected for varying excitation fields over an area that includes the write pole, and the magnetic field is derived from the ODMR spectrum using a high density NV film. In another embodiment, the magnetic field produced by the recording head 114 may be varied while maintaining the excitation field constant and the ODMR signal is detected to determine the magnitude of the bias signal necessary to produce a desired magnetic field from the recording head 114. In another embodiment, the thermal device on the recording head 114 may be controlled to vary the heating of the layer of the magnetic recording medium or the layer of material with low thermal conductivity while maintaining the excitation field constant and the ODMR signal is detected to determine the magnitude of the bias signal necessary to produce the desired heating.

During measurement, PL 113 produced by the NV centers 112, illustrated by the dotted line, will be collected by the objective lens 122 and directed by the beam splitter 120 towards a detector 130. As illustrated, a spectral filter 124, such as a dichroic film, is positioned before the detector 130 to remove any reflected excitation illumination and to direct only the PL to the detector 130. The spectral filter 124, thus, may be a long-pass filter with a wavelength cut-off at, e.g., 580 nm, to filter out any remaining pump light. The detector 130 may be, e.g., a non-imaging photodetector, such as a silicon avalanche photodiode operating in the signal photon regime, which detects the optical intensity at a single spot. Alternatively a CCD camera can be used to detect the PL.

In addition, a radio wave frequency (RF) antenna 126 is positioned to provide an excitation field to the crystal 110. The RF antenna 126 may produce a varying excitation field, e.g., that may be controlled to sweep the frequency in a continuous or stepped manner. A continuous or pulsed excitation field produced by the RF antenna 126 may have a power of, e.g., 1 W and a frequency ranging from 1 GHz to 5 GHz. The RF antenna 126 may also produce a constant excitation field. The excitation field produced by RF antenna 126 drives electron spin resonance which may be optically detected, e.g., ODMR, by detecting a drop in the spin dependent PL in response to the excitation illumination caused by electron spin resonance (ESR) of the nitrogen vacancy centers. The ODMR may be detected while varying the excitation frequencies of the excitation field while holding the magnetic field produced by the recording head 114 constant, while holding the excitation frequency of the excitation field constant while varying the magnetic field produced by the recording head 114, or while varying both the excitation frequencies of the excitation field and the magnetic field produced by the recording head 114.

The detector 130 is connected to a computer 140 and the computer 140 receives, stores, and analyzes the optically detected data provided by the detector 130, along with the excitation frequencies provided by RF antenna 126 associated with the data. The computer 140 includes a processor 142 with memory 144, as well as a user interface including e.g., a display 146 and input devices 148. A non-transitory computer-usable storage medium 150 having computer-readable program code embodied may be used by the computer 140 for causing the processor 142 to control the optical metrology device 100 and to perform the functions including the analysis described herein. The data structures and software code for automatically implementing one or more acts described in this detailed description can be implemented by one of ordinary skill in the art in light of the present disclosure and stored, e.g., on a computer readable storage medium 150, which may be any device or medium that can store code and/or data for use by a computer system such as processor 142. The computer-usable storage medium 150 may be, but is not limited to, magnetic and optical storage devices such as disk drives, magnetic tape, compact discs, and DVDs (digital versatile discs or digital video discs). A communication port 152 may also be used to receive instructions that are used to program the computer 140 to perform any one or more of the functions described herein and may represent any type of communication connection, such as to the internet or any other computer network. Additionally, the functions described herein may be stored in memory 155 or embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

As illustrated, the computer 140 may be coupled to the recording head 114, via a probe card 132 which is connected to the recording head 114 using one or more probes 134, which may be, e.g., pogopins, probes, or other contacts such as wires that are wire bonded. The probe card 132 may be coupled to a biasing source 131 that provides a bias signal, such as a current or voltage signal, which is provided to the recording head 114 via the probe card 132 and causes the recording head 114 to produce a magnetic field. The biasing source 131 may be connected to and controlled by the computer 140. The computer 140, thus, may control the magnetic field produced by the recording head 114, e.g., by controlling the bias signal provided to the recording head. The biasing source 131 may provide a plurality of bias signals with different levels to the recording head 114. Accordingly, the recording head 114 may be controlled via the biasing source 131 to produce a constant magnetic field, e.g., while the excitation field is varied, or to produce a varying magnetic field, while the excitation field is held constant (or varied). The varying magnetic field produced by the recording head 114 may vary continuously or in a stepped manner. The computer 140 may cause the biasing source 131 (or another biasing source) to further control any other desired features of the recording head 114, such a thermal device, e.g., a high intensity light source, on the recording head 114, when the recording head 114 is, e.g., a HAMR write head. Accordingly, the recording head 114 may be controlled via the biasing source 131 to produce a constant heat level, e.g., while the excitation field is varied, or to produce varying heat levels, while the excitation field is held constant (or varied). Additionally, when the recording head 114 includes a Dynamic-Flying Height (DFH) device, one of the probes 134 of the probe card 132 may be used to provide current to the microactuator device from a second circuit in the current or voltage source that is connected to the computer 140. Write heads use a DFH device as an adjustment mechanism to internally bias the write pole closer to or further from the air bearing surface. The DFH device is typically in the form of a heater incorporated into the write head structure, with additional contact pads for external connection. By applying a bias to the additional contact pads via the probe card 132, the position of the write pole can be adjusted towards or away from the air bearing surface of the write head. By adjusting the position of the write pole via the DFH device, the recording head 114 may be measured at different temperatures and/or vertical displacement from the crystal 110.

Additionally, when the recording head 114 includes a microactuator device, one of the probes 134 of the probe card 132 may be used to provide current to the microactuator device. The source of the current may be a second circuit in the current or voltage source connected to the computer 140. Write heads use a microactuator device as an adjustment mechanism to move the write pole in the cross-track direction to better align the write pole to the lands of a disk that is being written to. The microactuator device is incorporated into the write head structure, which includes additional contact pads for external connection. By applying a bias to the additional contact pads via the probe card 132, the position of the write pole can be adjusted in the cross-track direction. By adjusting the position of the write pole via the microactuator device during measurement with the device, the performance of the microactuator may be verified and the characteristics of the recording head 114 may be measured at different write pole positions.

The computer 140 is further coupled to control the RF antennab 126 to provide a desired excitation field (or varying excitation field) to the crystal 110 during measurement.

As discussed above, an NV center in diamond is a naturally occurring or technically created impurity in a diamond crystal where a Nitrogen atom replaces a Carbon atom creating a vacancy next to the Nitrogen atom. Nitrogen vacancy centers may be created in a diamond crystal, e.g., using a type-Ib HPHT single-crystal sample that is initially embedded with nitrogen impurities. For example, nitrogen impurities may be embedded by irradiation with a an ion-beam, e.g. $N_2^+$ ions at 5 keV, in case of a very high purity diamond film or by an electron beam in case the diamond film already has nitrogen impurities and annealing, e.g., for 2 hours at 850° C. The density of the NV centers within the crystal film may be controlled, e.g., by controlling the applied irradiation dose, or using appropriate masking techniques. For example, an ion beam fluence of $10^{11}$ cm$^2$ can result in density of $8\times10^{10}$ NV cm$^{-2}$. Moreover, by controlling the energy of the implantation as well as the annealing process the depth of the NV centers implanted in the crystal may be controlled.

Figure 2:
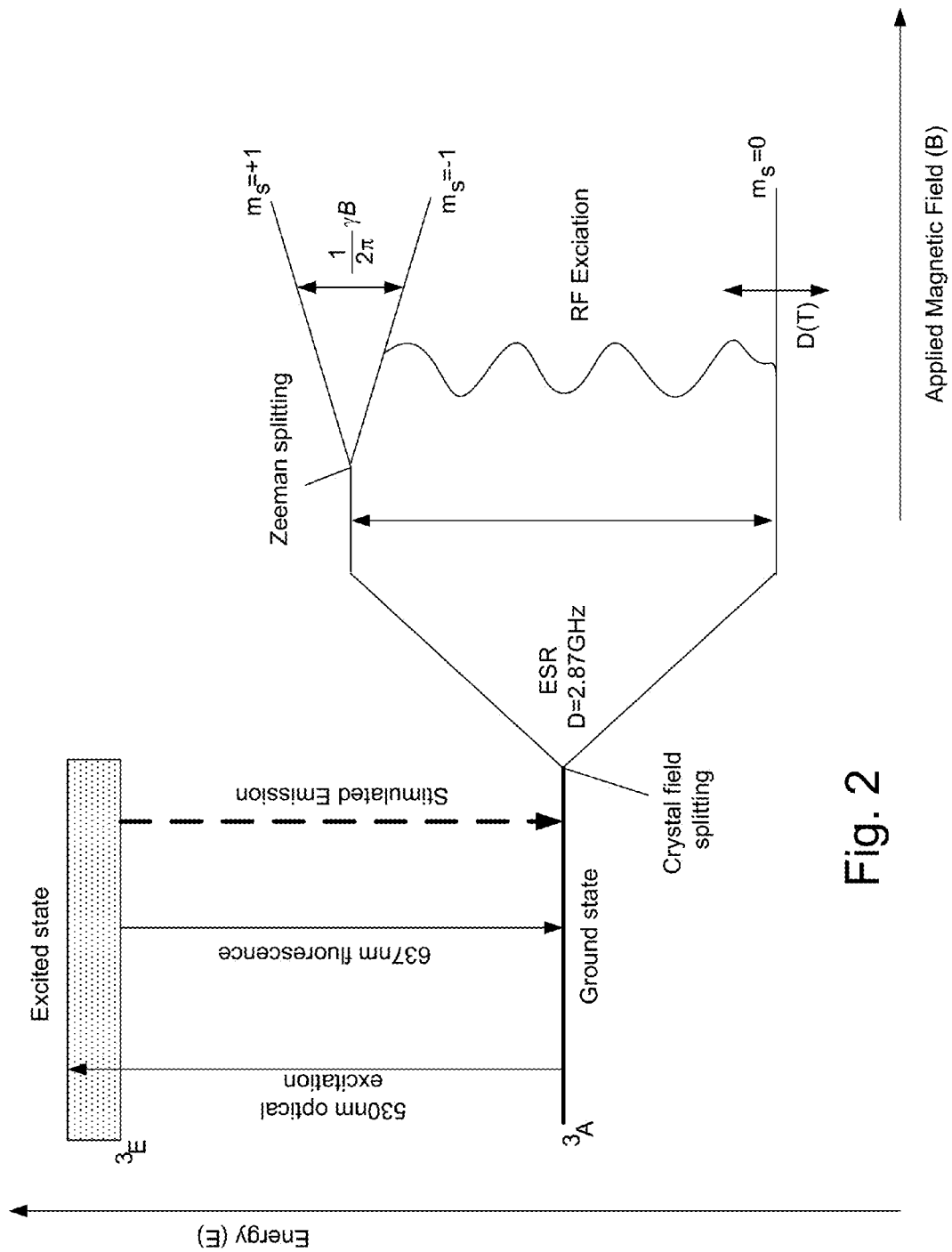
FIG. 2 schematically illustrates the energy levels of a negatively charged nitrogen vacancy center in a diamond crystal.

FIG. 2 schematically illustrates the energy levels of a negatively charged NV center in a diamond crystal. An NV center may be optically excited, e.g., with excitation illumination having a wavelength range from 460 nm to 580 nm, which yields an intense fluorescence emission from the NV center with lifetimes in the millisecond range. For example, as illustrated, the NV center may be excited with a laser at a wavelength of 532 nm and in response will emit a broadband luminescence with a zero phonon line at 637 nm, at room temperature. FIG. 2 further illustrates the mechanism of stimulated emission, in which an electron in an excited state gives energy to an incoming photon and is forced to the ground state before it can create photoluminescence by spontaneous emission. The ground state of the NV center has an electron spin triplet structure with a zero-field frequency splitting of 2.87 GHz between the $m_S=0$ and the degenerate $m_S=\pm1$ states. In the absence of an external magnetic field, e.g., from the recording head 114, a drop of luminescence intensity is present at an excitation frequency of 2.88 GHz due to the induced change in populations of $m_S=0$ and $m_S=\pm1$ spin sublevels. Thus, the location of the NV center may be identified by an optically detected zero field magnetic resonance at ~2.88 GHz which has its origin in the crystal-field splitting of energy sub-levels. The magnetic resonance occurs between the $m_S=0$ and $m_S=\pm1$ spin sub-levels of the spin triplet ground state $^3A_2$ and can be detected by either conventional electron paramagnetic resonance (EPR) or optically detected magnetic resonance (ODMR). The optical detection of the magnetic resonances of the NV center is enabled by the differing fluorescence of the $m_S=0$ and $\pm1$ spin projections, i.e. the fluorescence intensity is reduced when the spin system is in resonance due to the RF excitation.

In the presence of a magnetic field from the recording head 114, the resonance peak will split due to the Zeeman effect. As illustrated in FIG. 2, two resonance peaks may be identified, respectively corresponding to transitions between $m_S=0$ and $m_S=-1$, and between $m_S=0$ and $m_S=+1$ sublevels. The frequency of these resonance peaks is a function of the magnitude of the magnetic field and is called the Larmor frequency f given by $$f = \frac{1}{2\pi}\gamma B \qquad \text{eq. 1}$$

where $\gamma$ is the Gyromagnetic ratio and B the magnetic field, i.e. by measuring f, the magnetic field B may be determined. Thus, for magnetic field sensing applications, the magnetic field may be evaluated by measuring the Zeeman shifts of the NV center defect electron spin sub-levels through the optical detection of electron spin resonance (ESR), i.e., ODMR. The ODMR may be measured by detecting a decrease in the spin dependent PL caused by ESR of the NV centers while varying the excitation frequencies of the excitation field while holding the magnetic field produced by the recording head 114 constant, while holding the excitation frequency of the excitation field constant while varying the magnetic field produced by the recording head 114, or while varying both the excitation frequencies of the excitation field and the magnetic field produced by the recording head 114. One of the advantages of the use of NV center-based magnetometry is the possible combination of atomic-scale spatial resolution with high magnetic field sensitivity, e.g., below 10 nT Hz$^{-1/2}$, even under ambient conditions.

As illustrated in FIG. 2, the $m_S=0$ spin state is dependent on temperature D(T), and consequently the ESR frequency is temperature dependent. Moreover, the PL intensity ($I_{PL}$) of an NV center and the relative $I_{PL}$ difference between its spin states (ESR contrast), which strongly decrease above 550° K, may be used to measure temperature. Accordingly, one or more NV centers may serve as a nano-scale thermometer with sensitivities on the order of 100 mK/Hz between room temperature and 700° K. The high sensitivity and wide range of operating temperatures make NV centers an attractive candidate for a variety of thermo-sensing applications such as diamond-based scanning thermal microscopy. The impact of temperature versus magnetic field on the ESR spectrum may be distinguished using a pulsed RF excitation field with an appropriate pulse sequence (spin echo technique), as opposed to a continuous-wave RF excitation field. The thermal device of the recording head 114 may be controlled via the biasing source 131 to produce a constant temperature while the excitation frequency of the excitation field is varied or to produce different temperatures while holding the excitation frequency of the excitation field constant, or while varying both the temperature produced by the thermal device of the recording head 114 and the excitation frequencies of the excitation field.

In addition, the PL of an NV center may be turned "off" in time, when the 532 nm excitation pulse, e.g., with a duration of 60 ps, is followed by a longer wavelength pulse e.g. 775 nm and duration 3.2 ns, of sufficient intensity. This mechanism is known as Stimulated Emission Depletion (STED). Alternatively, STED with CW or quasi CW illumination may be employed. Spatial resolution may be improved using STED to functionally switch off a portion of NV centers, e.g., STED microscopy. For example, STED microscopy can be implemented by combining the excitation been with depletion illumination that has a focal intensity distribution $I_{STED}$ featuring a central zero intensity, such as a disk shape. The depletion illumination is coincident with the excitation illumination on the crystal film. Overlapping the Airy disk (Point Spread Function) of the excitation illumination having an intensity $I_S$ with the ring shaped depletion illumination and enforcing $I_{STED} \gg I_S$ switches off the NV centers covered by the Airy disk (diffraction limited) of the excitation illumination except for those at the depletion illumination minimum where $I_{STED} < I_S$. Thus, the Airy disk of the excitation illumination may be ignored when calculating the spot size in which NV centers may still be "on," i.e., responsive to the excitation illumination, and therefore, the effective point-spread function (PSF) of the system is no longer diffraction limited. Although the resolution Dx,y scales with the wavelength, adjusting $I^{max}$, the depletion illumination maximum, squeezes the STED SPSF (Stimulated Point Spread Function) continuously, and therefore wavelength is not a limiting factor. An advantageous property of the use of depletion illumination is that when scanned over the crystal film together with the excitation illumination, the ring-shaped depletion light intensity enables a reduced number of NV centers, e.g., a single NV center, to fall within the ring minimum. The stimulated point spread function determines the effective PL detection resolution, i.e., it is a characteristic of the apparatus and determines the minimum distance between two NV centers where the two NV centers can still be discriminated. All other NV centers are switched "off" by the depletion illumination or simply not excited by the excitation illumination. Thus, with the use of a depletion illumination, NV centers may be resolved individually, thereby further improving the spatial resolution of measurements, and may obviate the need to physically produce relative movement between the crystal with NV centers and the recording head to produce a two dimensional scan of the recording head.

Additionally, if desired, Ground State Depletion (GSD) may be used, as opposed to STED. Similar to STED, GSD uses depletion illumination to functionally switch off a portion of NV centers, but unlike STED, GSD uses the same wavelength for the excitation illumination and the depletion illumination.

Thus, one or more NV centers in a diamond film may be used to measure the write field of a recording head with nano-meter spatial resolution making use of the optically detected Electron Spin Resonance (ODMR), which frequency spectrum depends linearly on the magnetic field. Accordingly, characteristics of the recording head, including efficiency of the recording head, the strength of the magnetic field and physical dimensions of the write pole may be measured. This may be carried out by exercising the write portion of the recording head with a write current, which can be a DC or an AC current, to produce the magnetic field at the write pole. For example, the efficiency of the recording head may be determined by varying the bias signal to the recording head to vary the magnetic field while maintaining the excitation field at a constant frequency to determine the relationship between the applied bias signal and resulting magnetic field as provided by equation 1. In another example, the strength of the magnetic field may be determined for any scanned position based on the frequency of these resonance peaks, as provided by equation 1. Additionally, one or more NV centers in a diamond film may be used to measure the near-field power of a nano aperture in a recording head used in thermally assisted magnetic recording with nano-meter spatial resolution making use of temperature dependence of the optically detected Electron Spin Resonance or the temperature dependency of the PL intensity. Moreover, the efficiency of the thermal device in the recording head may be determined by varying the bias signal to the thermal device to vary the temperature while maintaining the excitation field at a constant frequency to determine the relationship between the applied bias signal and resulting heat.

Thus, a characteristic of the recording head 114 may be determined based on the ESR as measured by the detector 130, the frequency of excitation field produced by RF antenna 126, and the bias applied to the recording head 114 by the biasing source 131 to control the magnetic field and/or the heat produced by the thermal device. For example, a graph may be generated for the excitation field with respect to the bias signal. The excitation field may be fixed and the bias signal may be swept to vary the magnetic field or heat produced by the recording head, or the bias signal may be fixed and the excitation field swept. This process may be repeated at multiple levels of the fixed excitation field or the fixed bias signal and the magnetic field determined from the ESR, e.g., based on equation 1. Additionally, an external thermal device may be used to calibrate the ESR with respect to heat for one or more excitation frequencies of the RF antenna 126, and the heat produced by, e.g., a HAMR recording head 114, at one or more bias levels may be determined by measuring the ESR.

Figure 3:
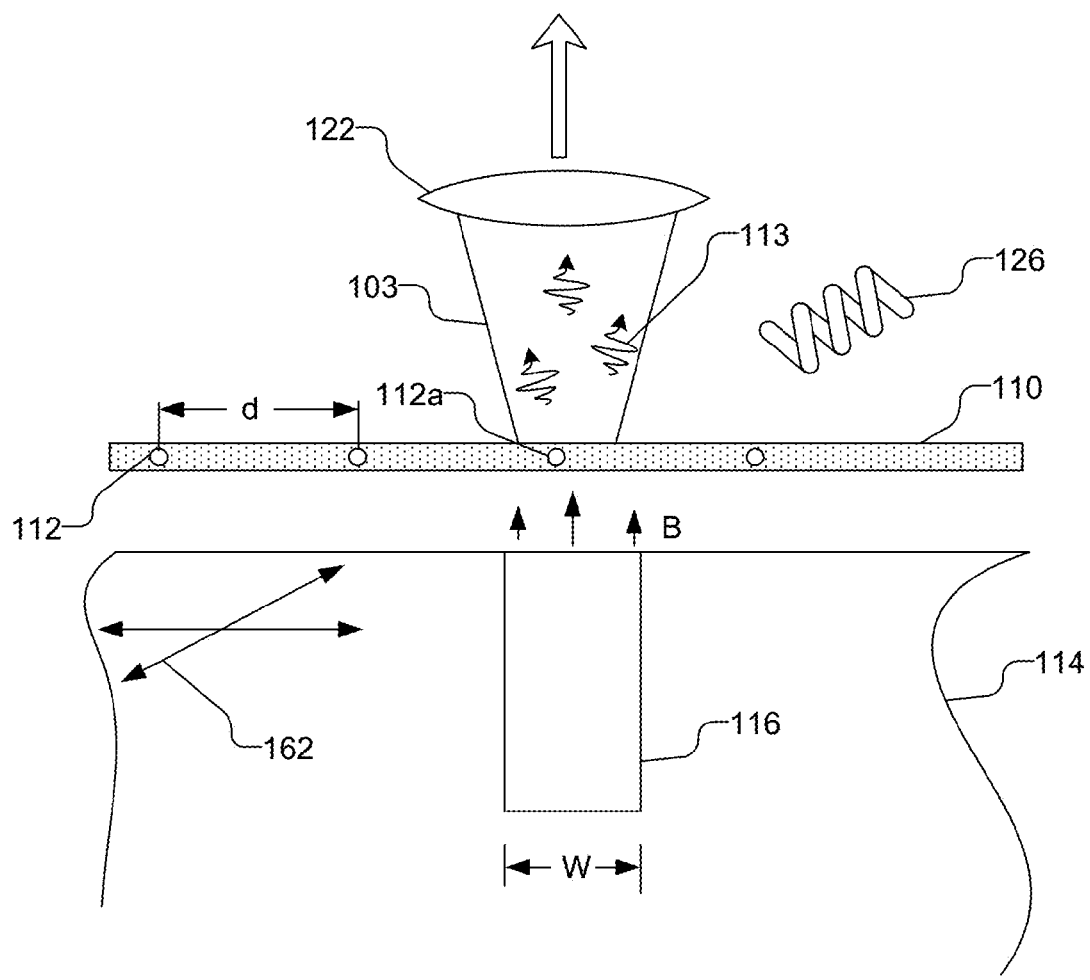
FIG. 3 schematically illustrates a diamond film with a plurality of nitrogen vacancy centers that is positioned to be in a magnetic field produced by a write pole from a recording head.

FIG. 3, by way of example, schematically illustrates a diamond film 110 with a plurality of NV centers 112 and that is positioned to be in a magnetic field B produced by a write pole 116 from a recording head 114. As discussed above, a light source 102 (shown in FIG. 1) produces excitation illumination 103 that is focused by objective lens 122 onto the diamond film 110 while an external RF excitation field is produced by the RF antenna 126 with varying excitation frequencies or pulse sequence. In response to the excitation illumination 103, the NV center 112a produces spin dependent PL 113 that is collected by the objective lens 122 and provided to the detector 130 (shown in FIG. 1). The Optically Detected Spin Resonance (ODMR) may be measured by detecting a decrease in the spin dependent PL 113 caused by electron spin resonance (ESR) of the NV centers at varying excitation frequencies of the excitation field. If desired, the magnetic field of the recording head 114 may be varied while maintaining a constant frequency of the excitation field (or varying the frequency of the excitation field) while measuring ODMR.

As illustrated in FIG. 3, the write pole 116 has a width W, while the density of the NV centers 112 in the diamond film 110 is such that adjacent NV centers are separated by a distance d that is greater than the width W of the write pole 116, i.e., d>W. In such a configuration, a single NV center may be positioned over the write pole 116, as illustrated. Relative movement between the recording head and the diamond film 110 may be produced in two dimensions, e.g., by moving the recording head with respect to the diamond film 110, thereby scanning a single NV center over the recording head in two dimensions, as illustrated by arrows 162. The ODMR may be measured by detecting a decrease in the spin dependent PL 113 caused by electron spin resonance (ESR) of a single NV center at varying excitation frequencies of the excitation field and/or varying magnetic fields of the recording head as the NV center is scanned over the recording head in two dimensions. Accordingly, characteristics of the recording head 114 may be measured with nano-meter spatial resolution including the efficiency of the recording head, dimensions of write pole 116 and strength of the magnetic field B.

Figure 4:
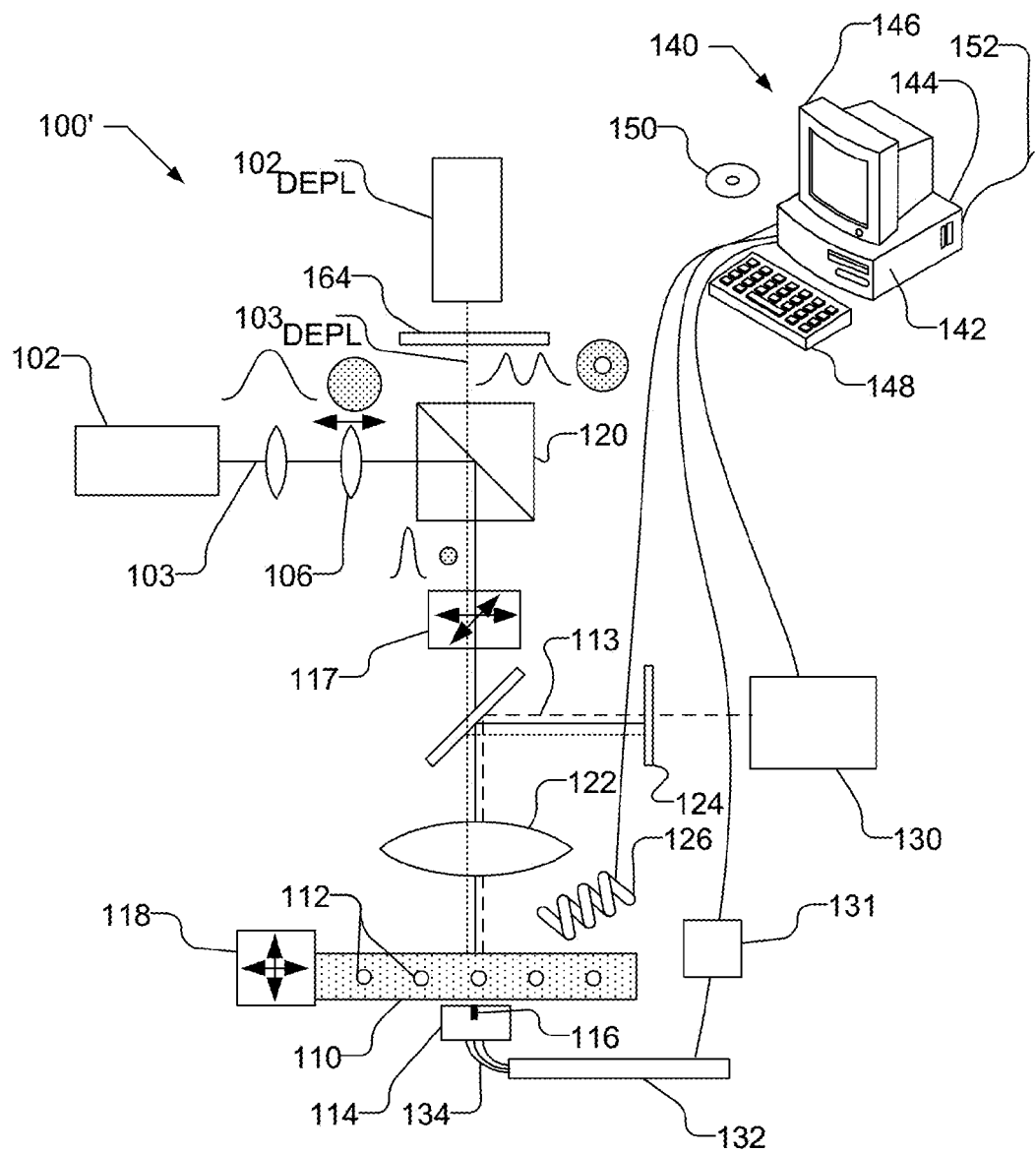
FIG. 4 illustrates an optical metrology device that uses Stimulated Emission Depletion.
Figure 5:
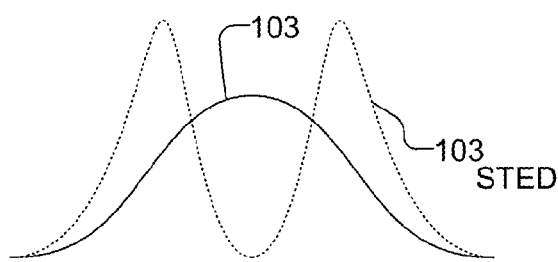
FIG. 5 illustrates the point spread function of excitation illumination and depletion illumination.
Figure 6:
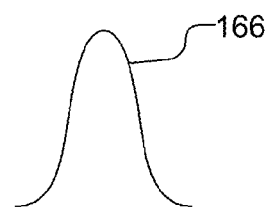
FIG. 6 illustrates the effective point spread function of the combined excitation illumination and depletion illumination from FIG. 5.

FIG. 4 illustrates an optical metrology device 100' that is similar to the optical metrology device 100, shown in FIG. 1, like designated elements being the same, but that uses Stimulated Emission Depletion (or GSD) as discussed above. As illustrated, optical metrology device 100' includes a second light source $102_{DEPL}$ that produces depletion illumination $103_{DEPL}$, with the same or different wavelength in the case of GSD or STED, respectively, and that is coincident on the diamond film 110 with the excitation illumination 103 from light source 102. The light source 102 produces excitation illumination 103 that has a Gaussian point spread function and produces a relatively large diffraction limited spot on the diamond film 110. FIG. 5, by way of example, illustrates the Gaussian point spread function of the excitation illumination 103 with a solid line. The second light source $102_{DEPL}$ produces light that passes through a vortex phase plate 164 to produce a ring shaped beam that has a central zero intensity at the focal plane. FIG. 5, by way of example, illustrates a ring shaped point spread function distribution of the depletion illumination $103_{DEPL}$ which is coincident with the excitation illumination 103. The depletion illumination $103_{DEPL}$ quenches PL in the NV centers 112 in the diamond film 110 that are off-center, so that the off-center NV centers only contribute a constant background, which may be subtracted from the ODMR signal, thereby providing a signal from only the NV centers in the center of the depletion illumination $103_{DEPL}$. FIG. 6 illustrates the effective point spread function 166 of the combined excitation illumination 103 combined with the depletion illumination $103_{DEPL}$. The coincident excitation illumination 103 and depletion illumination $103_{DEPL}$ may be scanned over the diamond film 110 to measure characteristics of the recording head 114 in two dimensions, e.g., using one or more mirrors 117 in the beam path.

In the case of using GSD, the depletion illumination $103_{DEPL}$ may have a wavelength of 532 nm, with increased power. For example, a reduction in the photoluminescence may be achieved for depletion illumination $103_{DEPL}$ with power greater than 2 MW/cm$^2$. The depletion illumination $103_{DEPL}$ may be continuous (CW) or pulsed excitation, with a pulse width of, e.g. 150 ps, where a pulsed depletion illumination $103_{DEPL}$ results in stronger photoluminescence reduction.

Figure 7:
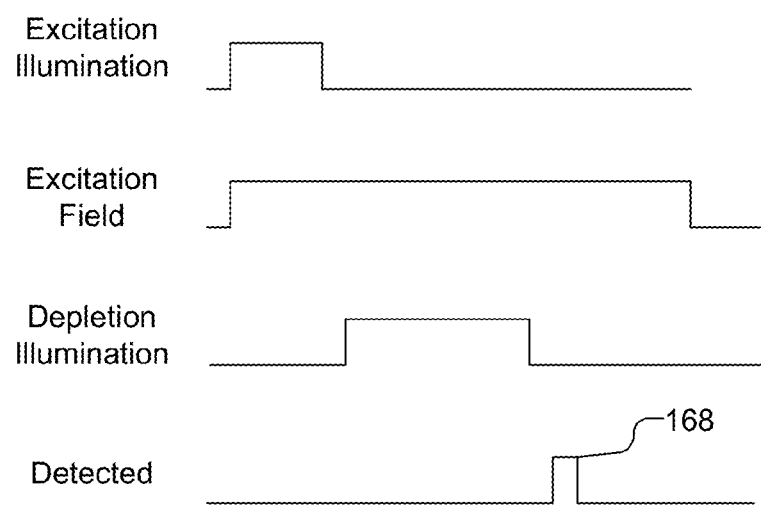
FIG. 7 illustrates several waveforms used to measure Optically Detected Spin Resonance using depletion illumination.

FIG. 7, by way of example, illustrates several waveforms that may be used to measure ODMR using depletion illumination. As illustrated, a pulse of excitation illumination is provided along with the excitation field and followed by a pulse of depletion illumination. The RF excitation field need not be pulsed and may always be on, and one or both of the excitation field and the magnetic field produced by the recording head 114 may be varied. The intensity of the depletion illumination is much greater than the intensity of the excitation illumination in the case of case of GSD or has a longer wavelength in case of STED. The PL signal 168 is detected after the pulsed depletion illumination.

Figure 8:
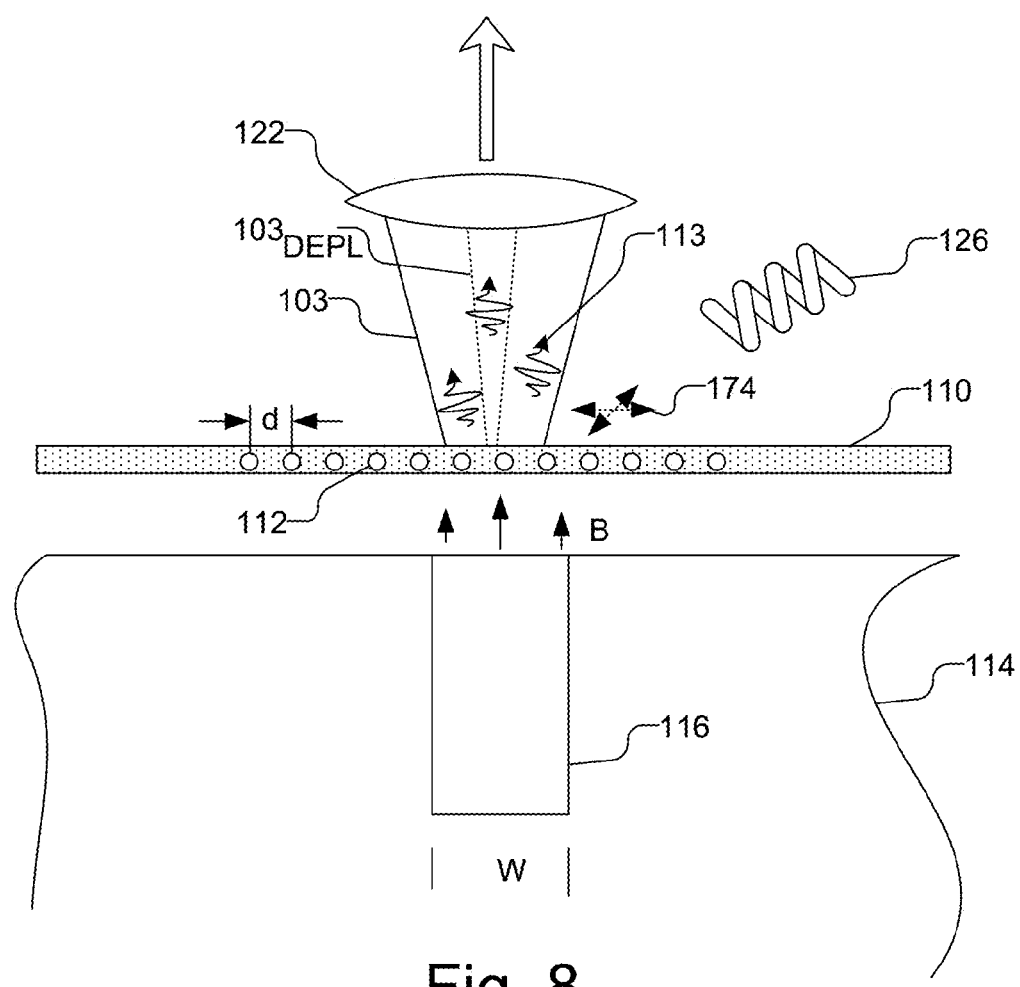
FIG. 8 schematically illustrates the use of depletion illumination to measure Optically Detected Spin Resonance from a diamond film with a plurality of nitrogen vacancy centers that is positioned to be in a magnetic field produced by a write pole from a recording head.

FIG. 8 schematically illustrates the measurement of ODMR from a diamond film 110 with NV centers 112 similar to FIG. 3, but uses depletion illumination $103_{DEPL}$, e.g., for either STED or GSD, and the diamond film 110 as an increased density of NV centers 112. As illustrated in FIG. 8, the density of the NV centers 112 in the diamond film 110 may be such that adjacent NV centers are separated by a distance d that is less than the width W of the write pole 116, i.e., d<W. The density of NV centers may be chosen so that a plurality of NV centers, e.g. 10×10 NV centers, is located under the write pole 116. The coincident excitation illumination 103 and depletion illumination $103_{DEPL}$ enables a reduced number of NV centers to be resolved, e.g., only NV centers that fall within the ring minimum of the depletion illumination $103_{DEPL}$ are resolved. The coincident excitation illumination 103 and depletion illumination $103_{DEPL}$ may be scanned in two dimensions over the diamond film, as illustrated by arrows 174, e.g., using an arrangement of mirrors in the beam path, thereby obviating the needs for an actuator to produce relative movement between the recording head and the diamond film 110. The ODMR may be measured by detecting a decrease in the spin dependent PL 113 caused by electron spin resonance (ESR) of the NV center(s) that fall within the ring minimum of the depletion illumination $103_{DEPL}$ at varying excitation frequencies of the excitation field and/or varying magnetic fields produced by the recording head 114 as excitation illumination 103 and depletion illumination $103_{DEPL}$ are scanned over the recording head in two dimensions. Accordingly, characteristics of the recording head may be measured with nano-meter spatial resolution including dimensions of write pole 116 and strength of the magnetic field B.

Figure 9:
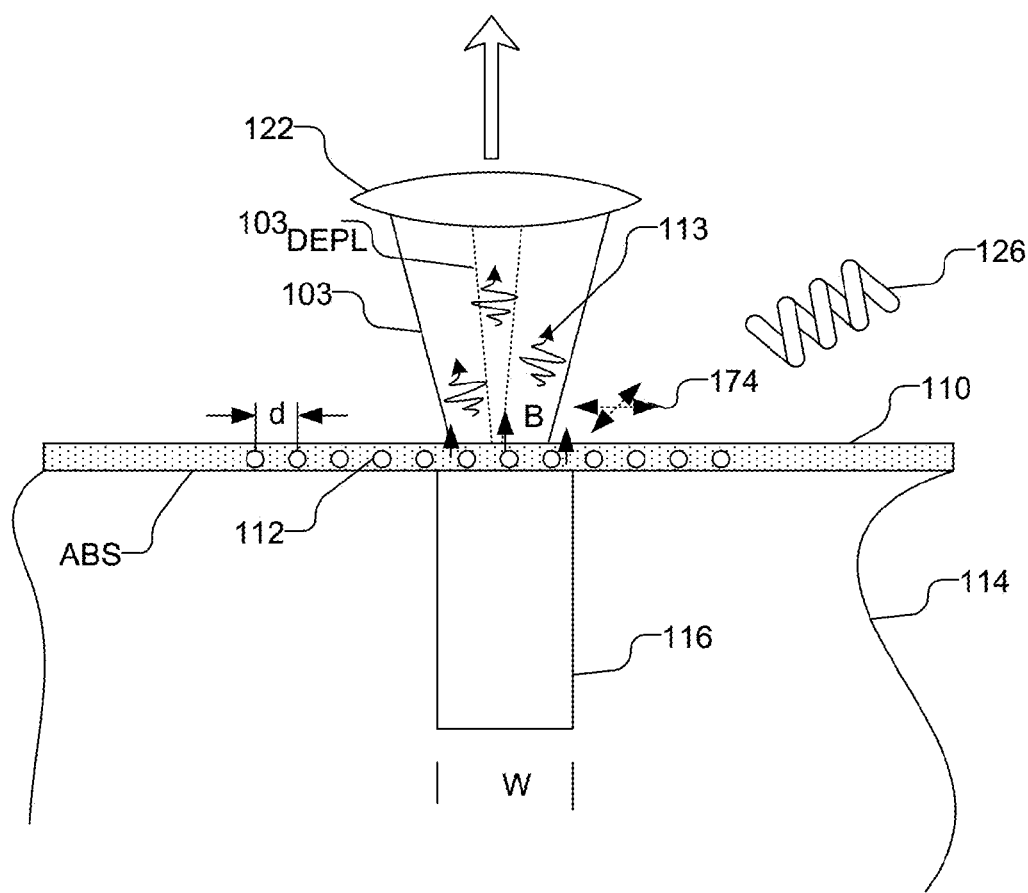
FIG. 9 schematically illustrates the use of depletion illumination to measure Optically Detected Spin Resonance from a diamond film with a plurality of nitrogen vacancy centers that is in contact with the air bearing surface of the recording head.

If desired, the diamond film 110 may be in direct contact with the recording head 114, e.g. in contact with the Air Bearing Surface (ABS) of the recording head. For example, a diamond film 110 with a relatively high density of NV centers 112, e.g., such that there are a plurality of NVC centers located under the write pole, may be directly deposited on the ABS of the recording head. FIG. 9 schematically illustrates the measurement of ODMR from a diamond film 110 with NV centers 112, similar to that shown in FIG. 8, but with the diamond film 110 attached to the ABS of the recording head 114, i.e., directly coupled to or coupled to with one or more intervening layers. As discussed above, the coincident excitation illumination 103 and depletion illumination $103_{DEPL}$ may be scanned with respect to the recording head in two dimensions to measure ODMR at varying excitation frequencies of the excitation field and/or varying magnetic fields produced by the recording head 114 as excitation illumination 103 and depletion illumination $103_{DEPL}$ are scanned over the recording head in two dimensions.

Figure 10:
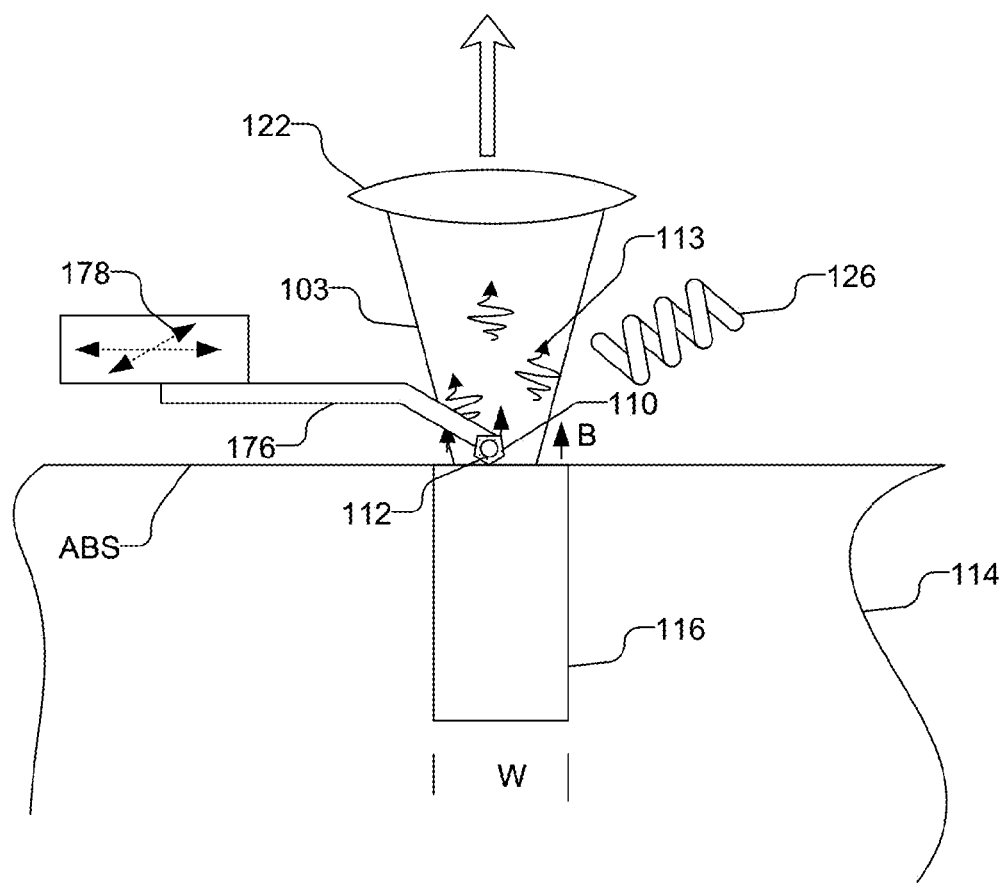
FIG. 10 schematically illustrates a diamond film with a nitrogen vacancy center that is on an Atomic Force Microscope arm positioned to be in a magnetic field produced by a write pole from a recording head.

FIG. 10 is similar to FIG. 3 and schematically illustrates the measurement of ODMR from a diamond film 110 with an NV center 112 held on the tip of an Atomic Force Microscope (AFM) arm 176 and that is in contact with the ABS of the recording head 114. As illustrated, the diamond film 110 may be a micron sized diamond particle that includes a single or several NV centers 112. The AFM arm 176 is scanned over the recording head 114 in two dimensions, as illustrated by arrows 178 and the PL 113 from the NV centers is collected. As the AFM arm 176 is scanned over the recording head 114, there is no need for depletion illumination. Thus, the ODMR may be measured from the NV center(s) 112 in the diamond film 110 positioned at the tip of the AFM arm 176, at varying excitation frequencies of the excitation field and/or varying magnetic fields produced by the recording head 114 as the AFM arm 176 is scanned over the recording head in two dimensions.

Figure 11:
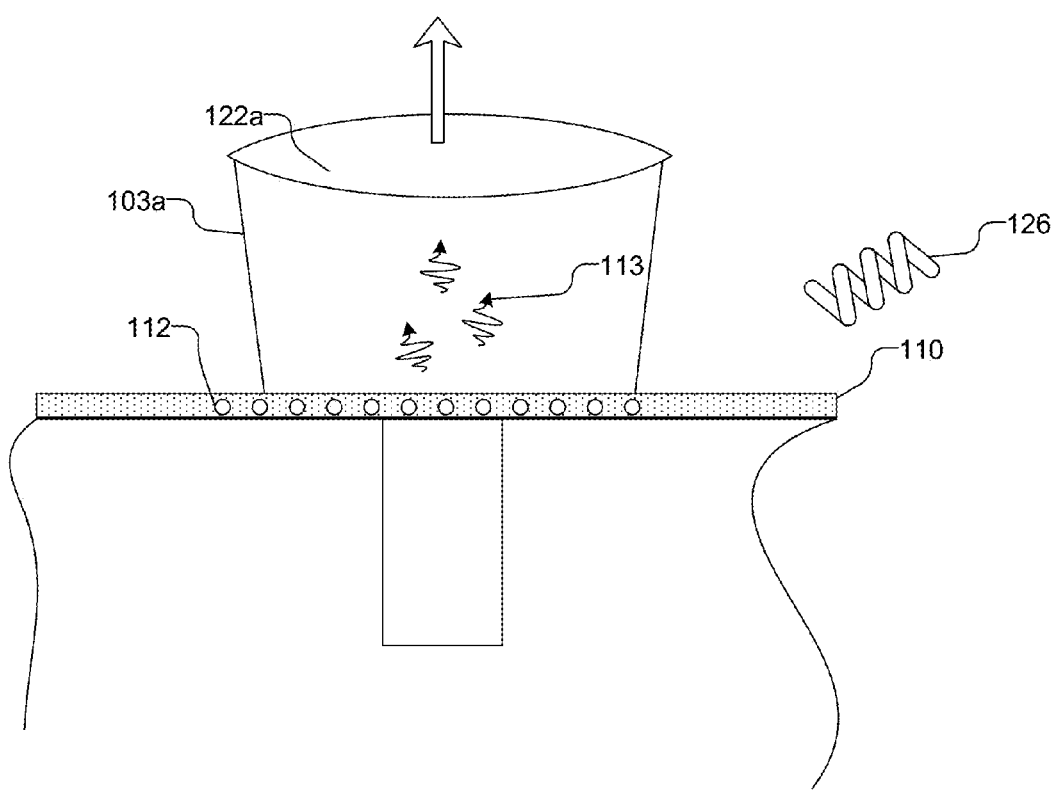
FIG. 11 schematically illustrates a diamond film with a matrix of evenly spaced nitrogen vacancy centers that is positioned to be in a magnetic field produced by a write pole from a recording head and that is illuminated with wide-field illumination.
Figure 33:
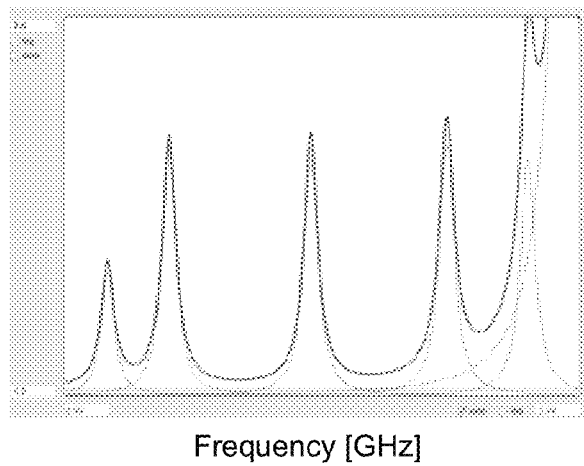
FIG. 33 is an ESR spectrum that may be generated while measuring a near field aperture and that may be evaluated to extract temperature information.

Additionally, a characteristic of a recording head may be determined by measuring the ODMR from a diamond film 110 that includes a matrix of evenly spaced NV centers having a known density. FIG. 11, by way of example, is similar to FIG. 3, and schematically illustrates the measurement of ODMR from a diamond film 110 with a matrix of evenly spaced NV centers 112 with a known density, but uses wide-field illumination 103a that is incident on the diamond film 110 and resulting PL is collected by lens 122a and an integrated PL is used. Wide field illumination, as used herein, refers to illumination used with micrsocopy having a homogeneously illuminated field of view to form an image, as compared to scanning a focused beam. The integrated PL over an area that covers the write pole (or near field aperture) is detected. The RF excitation field may be swept over a range of frequencies adequate for the write-field range to be measured or the temperature range in case the near-field power is measured. The detected PL signal will contain discrete resonance lines, similar to those illustrated in FIG. 15 (field measurement) or FIG. 33 (temperature), that can be mapped onto the known spatial distribution of the NV centers. Characteristics of the recording head may be determined from the measured ODMR and known density of the NV centers, i.e. a known distance between adjacent NV centers. For example, assuming the magnetic field is at a maximum at the write gap, the spatial distribution of the write field including magnetic write width may be determined from the discrete resonance lines that correspond to discrete locations in two dimensions of the NV centers. Accordingly, no scanning of the recording head or super-resolution techniques, such as STED or GSD, is required because wide-field illumination is employed as illustrated in FIG. 11.

Figure 12:
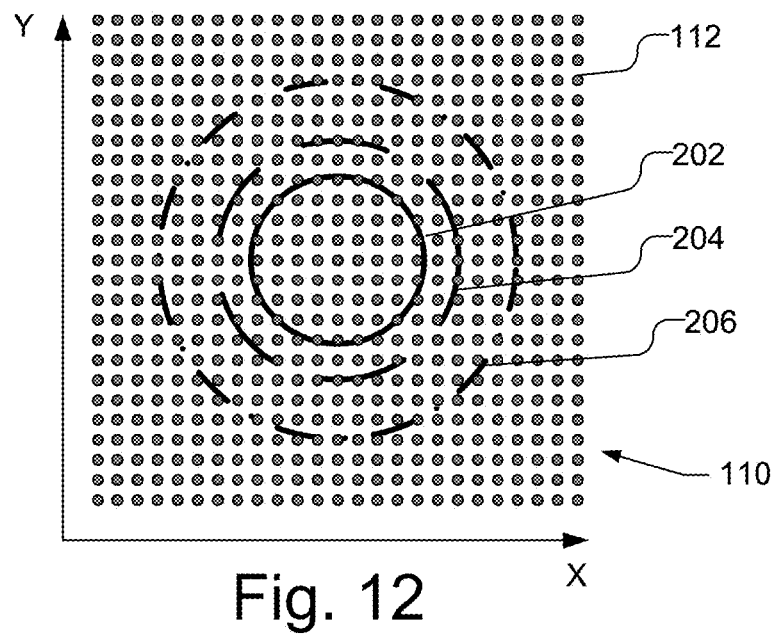
FIG. 12 illustrates a matrix of evenly spaced nitrogen vacancy centers in a diamond film having a density such that the distance between adjacent nitrogen vacancy centers is less than the width of a write pole.
Figure 13:
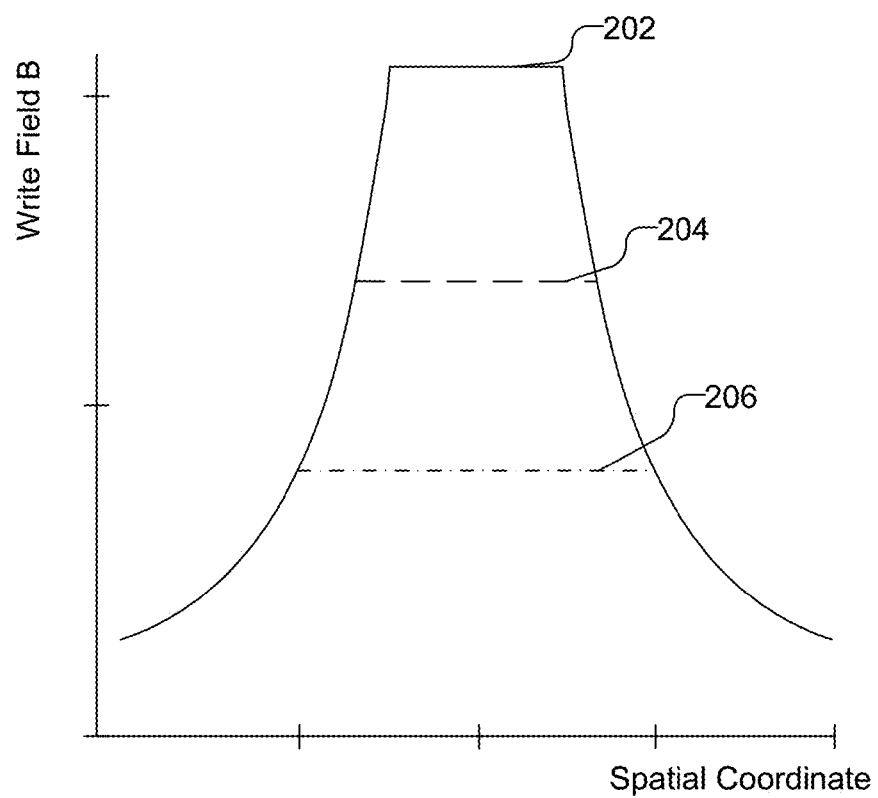
FIG. 13 illustrates an exemplary homogenous write field distribution of a write pole having radial symmetry and a maximum plateau.

FIG. 12, by way of example, illustrates a matrix of evenly spaced NV centers 112 in a diamond film 110, having a density such that the distance between adjacent NV centers 112 is less than the width of a write pole. As illustrated in FIG. 11, the matrix of evenly spaced NV centers 112 in the diamond film 110 is placed in a magnetic field produced by the write pole 116, e.g., by bringing the diamond film 110 into contact or near contact with the write pole 116. FIG. 13, by way of example, illustrates a homogenous write field distribution of a write pole 116 having radial symmetry and a maximum plateau. The spatial extent of different values of the write field, e.g., the field maximum 202, and field values 204 and 206, are illustrated in FIG. 12 as circles having the same reference numbers.

Figure 14A:
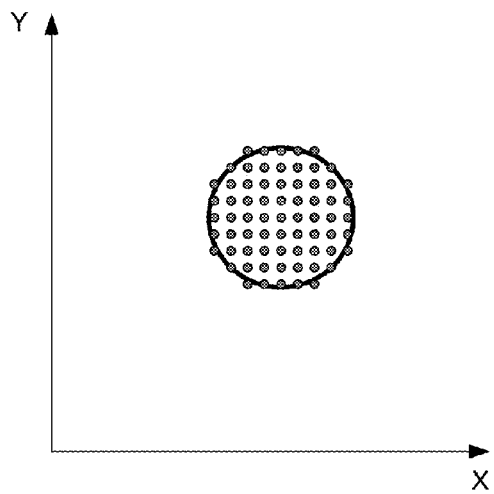
FIGS. 14A, 14B, and 14C illustrate nitrogen vacancy centers with the same resonance conditions when measuring ODMR in a homogenous write field distribution.
Figure 14B:
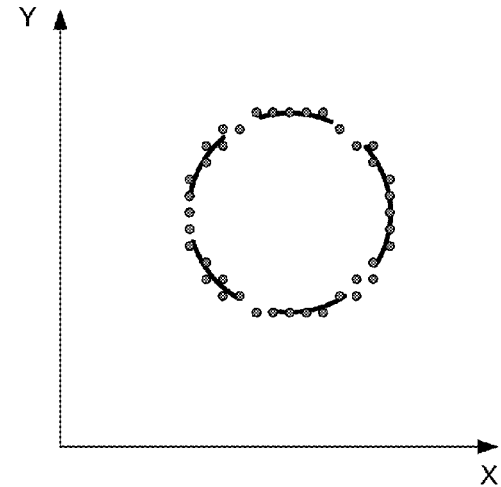
Figure 14C:
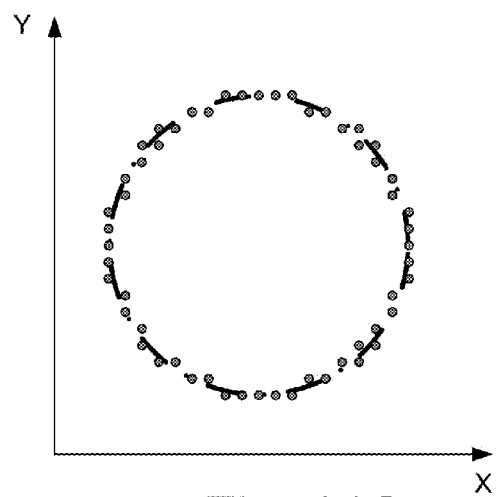

The NV centers enable optically detected electron-spin resonance (ODMR) under excitation with an external RF-field. By sweeping the frequency of the excitation field, the field distribution may be mapped in two dimensions according to the local resonance condition given by the local field magnitude as described in equation 1. By sweeping the magnetic fields produced by the recording head 114, the magnetic fields produced in response to different bias signals may be mapped according to the local resonance condition given by the local field magnitude as described in equation 1. For the illustrative homogenous write field distribution of FIG. 13 and a matrix of NV centers 112 as depicted in FIG. 12, the resonance condition of equation 1 is fulfilled for a plurality of NV centers at the maximum write field 202, as illustrated in FIG. 14A, and for NV centers on concentric circles for lower field values 204 and 206 in the case of a field distribution with rotational symmetry, as illustrated in FIG. 14B and FIG. 14C, respectively. Thus, FIGS. 14A, 14B, and 14C illustrate NV centers with the same resonance conditions when measuring ODMR in a homogenous write field distribution.

The ODMR response of an individual NV center may be difficult to measure using optical wide-field imaging due to the nano-meter spacing of NV centers, which is beyond the optical diffraction limit of the objective lens 122a in FIG. 11. However the integrated PL intensity emitted from the array of NV centers may be collected for varying RF-excitation frequencies and/or varying magnetic fields produced by the recording head 114. The integrated PL intensity may be written as follows.

$$SM(f_{RF}) = \sum_y \sum_x [A(f_{RF}, x, y)] \qquad \text{eq. 3}$$

Where SM is the integrated PL intensity, which is a function of the excitation frequency $f_{RF}$, and $A(f,x,y)$ is the PL intensity for a single NV center at position (x,y) in the NV center matrix at the excitation frequency $f_{RF}$.

Figure 15:
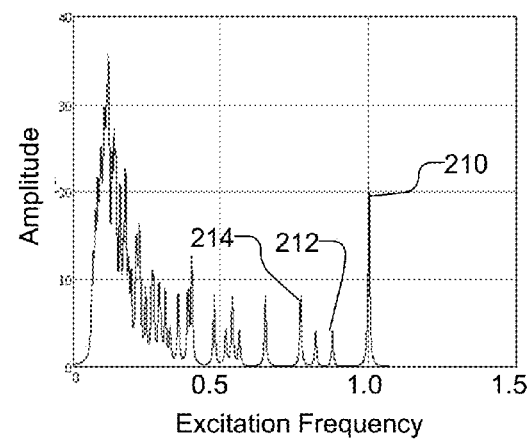
FIG. 15 illustrates an ESR spectrum with the amplitude of the integrated photoluminescence emitted from the matrix of nitrogen vacancy centers for a homogenous write field distribution with respect to various excitation frequencies.

FIG. 15, for example, illustrates an ESR spectrum with the amplitude of the integrated PL emitted from the matrix of NV centers shown in FIG. 12 for the homogenous write field distribution of FIG. 13 with respect to various excitation frequencies. As illustrated in FIG. 15, the result is a frequency spectrum with discrete resonance lines that can be attributed to the NV centers that are subject to the same resonance condition. For example, the peak 210 illustrated in FIG. 15 corresponds to the integrated PL intensity emitted from the NV centers shown in FIG. 14A, which have the resonance condition of equation 1 fulfilled at the maximum write field 202 illustrated in FIG. 13. In other words, the peak 210 in FIG. 15 is associated with the maximum write field 202. The frequency spectrum includes additional discrete resonance lines, e.g., 212 and 214, which may correspond to the NV centers illustrated FIGS. 14B and 14C, by way of example.

Thus, for the idealized case of the write field illustrated in FIG. 13 and for a given spacing and known single NV center PL-intensity, the write pole area, i.e. the area of the flat part of the field distribution that is related to the pole area, may be determined. For example, the integrated PL intensity for one spectral line may be divided by the known single NV center PL-intensity to determine the number of contributing NV centers. As the spacing of the NV centers is known, the area of the peak write field can be determined. Moreover, the magnitude of the peak write field may be deduced from the resonance frequency of the highest order resonance line 210 shown in FIG. 15 using equation 1.

Figure 16:
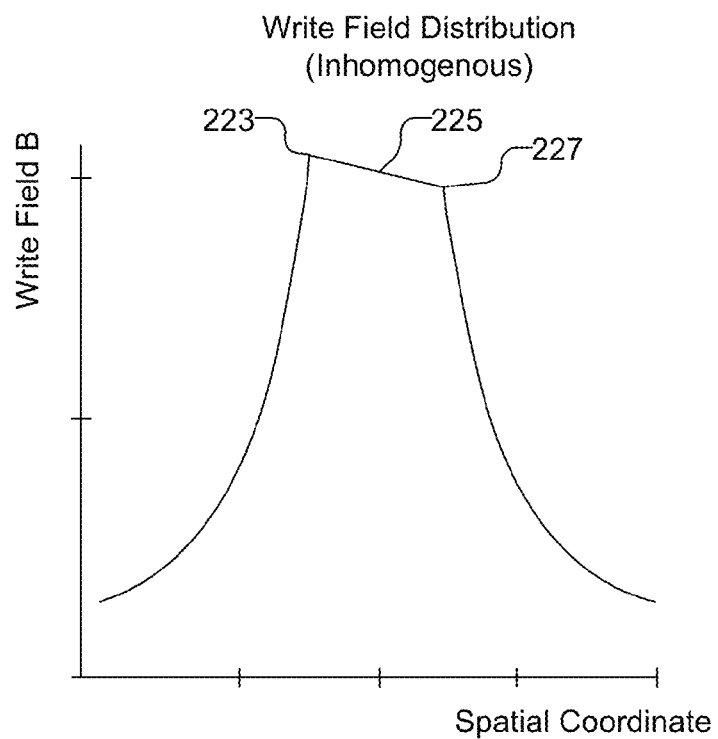
FIG. 16 illustrates an exemplary in-homogenous write field distribution of a write pole having radial symmetry.
Figure 17:
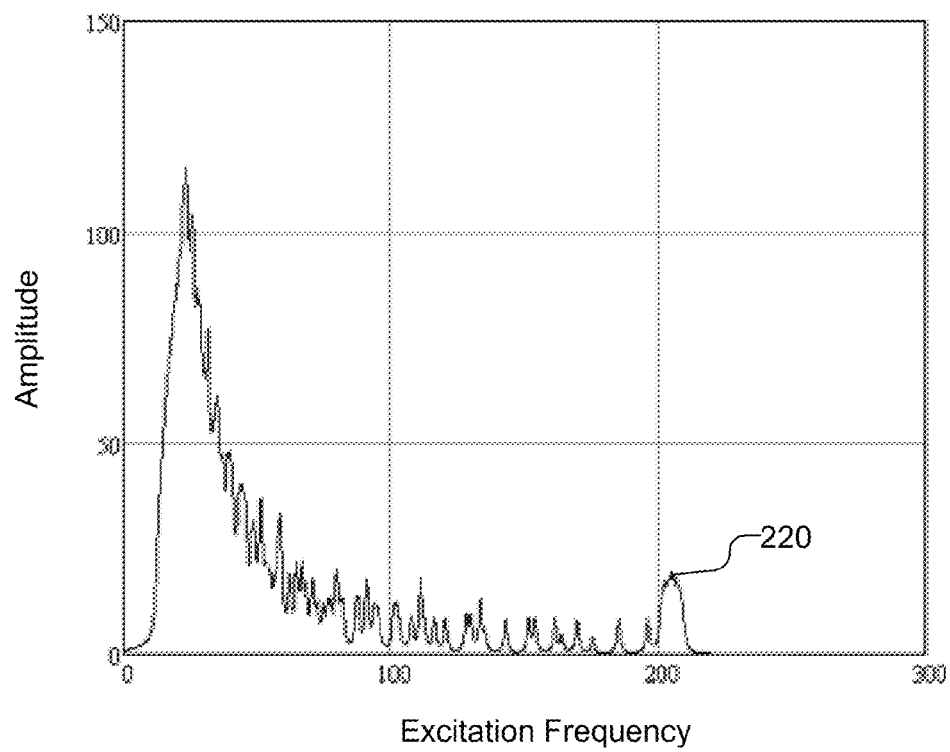
FIG. 17 illustrates an ESR spectrum with the amplitude of the integrated photoluminescence emitted from the matrix of nitrogen vacancy centers for an in-homogenous write field distribution with respect to various excitation frequencies.

FIG. 16 illustrates another write-field distribution, similar to that shown in FIG. 13, but that is in-homogenous with radial symmetry, which is more realistic than that illustrated in FIG. 13, as the peak write-field distribution in FIG. 16 varies linearly along the x-axis. FIG. 17 is an ESR spectrum illustrating the amplitude of the integrated PL emitted from the matrix of NV centers shown in FIG. 12 for the in-homogenous write field distribution of FIG. 16, with respect to various excitation frequencies. As can be seen, the spectrum of the integrated PL intensity has a broadened resonance peak 220 at an excitation frequency of approximately 205. FIG. 18 illustrates a magnified view of the resonance peak 220 from FIG. 17. As can be seen in FIG. 18, the broadened resonance peak 220 includes discrete resonance lines, which are related to discrete write field values, where the highest frequency line 222 is related to the maximum field at the pole edge. The amplitude of each isolated resonance line in FIG. 18 is proportional to the number of contributing NV centers and may be determined, e.g., by a multi Lorentz-Function fit. By way of example, FIG. 19A illustrates NV centers 112 having positions that correspond to the peak write field (223 in FIG. 16) and, thus, contribute to the resonance line 222 in FIG. 18. Similarly, FIG. 19B illustrates the NV centers 112 with positions that correspond to the write field 225 in FIG. 16) and, thus, contribute to the resonance line 224 in FIG. 18, and FIG. 19C illustrates the NV centers 112 with positions that correspond to the write field 227 in FIG. 16 and, thus, contribute to the resonance line 226 in FIG. 18. Thus, the discrete frequencies illustrated in the frequency spectra shown in FIG. 18 may be mapped onto the two-dimensional spatial distribution of the write field based on the known spacing of the NV centers. With the reasonable assumption that the highest field value is at the edge of the write pole, i.e., at the write gap, the spatial field distribution may be reconstructed by scaling the line order number in the frequency spectrum with the known distance between NV centers, where counting starts at the highest frequency. The spacing between the resonance lines reflects the field gradient, i.e. the larger the line separation the higher the field gradient. The sharp increase of the field gradient (indicated by the increased separation of resonance lines), for frequencies less than 200 in FIG. 18 coincides with the edge of the write pole and, consequently, the geometry can be extracted. By way of example, a preset static, or a dynamic threshold may be applied to the number of resonance lines to identify resonance lines associated with the edge of the write pole. For example, as illustrated in FIG. 18, there are 11 discrete resonance lines between, and including, peaks 222 and 226. If the distance between NV centers is known to be 20 nm, the spatial extent of the peak of the in-homogenous write field distribution (e.g., between 223 and 227 in FIG. 16) would be 200 nm. The spatial extent of the peak of the write field corresponds to the size of the write pole. Thus, the spatial distribution of the peak of the write field, and accordingly the diameter of the write pole, may be determined based on the maximum excitation frequency, the number of spectral lines associated with an edge of the write pole, and the known density of the nitrogen vacancy centers which determines the spatial relation of the spectral lines.

For a write field distribution with radial symmetry, as illustrated in FIGS. 13 and 16, the NV centers 112 contributing to ODMR at the same excitation field are on concentric circles with discrete radii determined by the discretization of the NV centers in the matrix. Thus, the write field profile may be reconstructed by mapping the number of the resonance line to the radius R considering the discrete grid points x, y of the NV center matrix and the write field $B_z$ as determined from equation 1. As the radius R is determined based on discrete grid points of the NV center matrix and the number of the resonance line in the frequency spectrum, the amplitude of the resonance line is not relevant.

Figure 20:
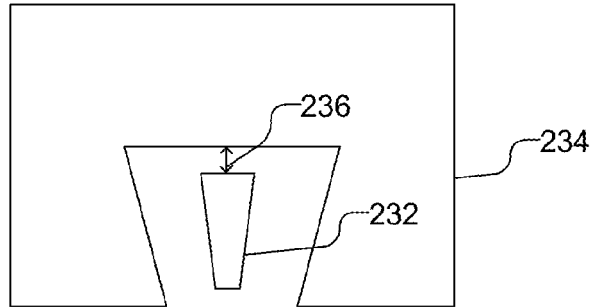
FIG. 20 illustrates a plan view of a portion of a recording head with write pole with a wrap-around shield.
Figure 21A:
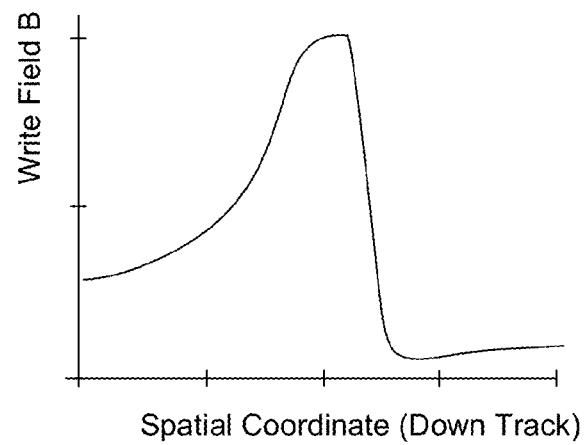
FIGS. 21A and 21B illustrate a write field profile of a recording head of FIG. 20 in the down track and cross track directions.
Figure 21B:
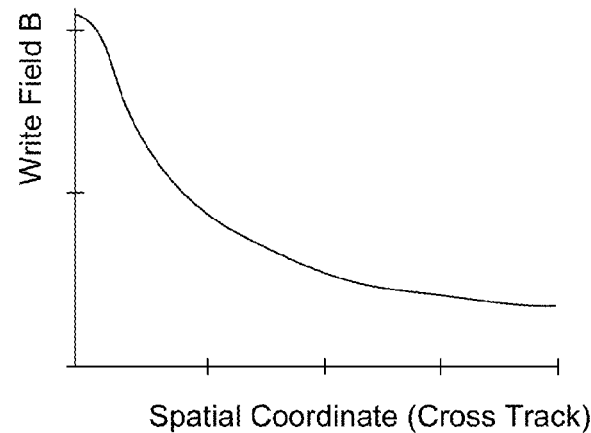
Figure 22:
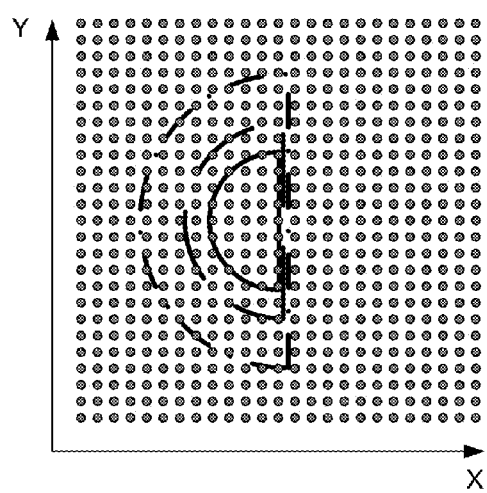
FIG. 22 illustrates a matrix of evenly spaced nitrogen vacancy centers in a diamond film overlying the write field from FIGS. 21A and 21B illustrated as semi-circles.
Figure 23A:
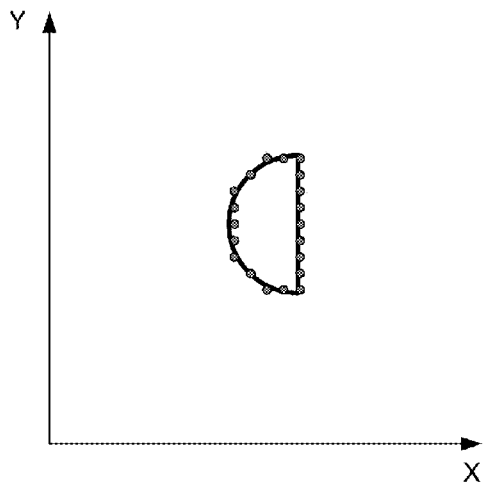
FIGS. 23A, 23B, and 23C illustrate nitrogen vacancy centers with the same resonance conditions when measuring ODMR in the write field distribution of FIGS. 21A and 21B.
Figure 23B:
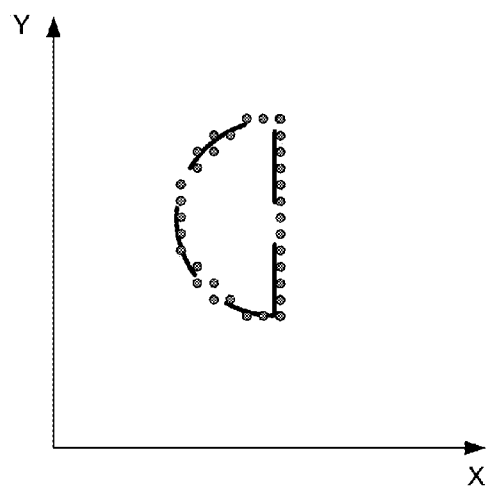
Figure 23C:
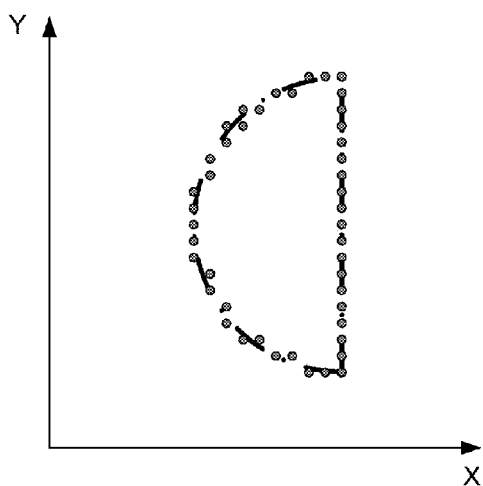
Figure 24:
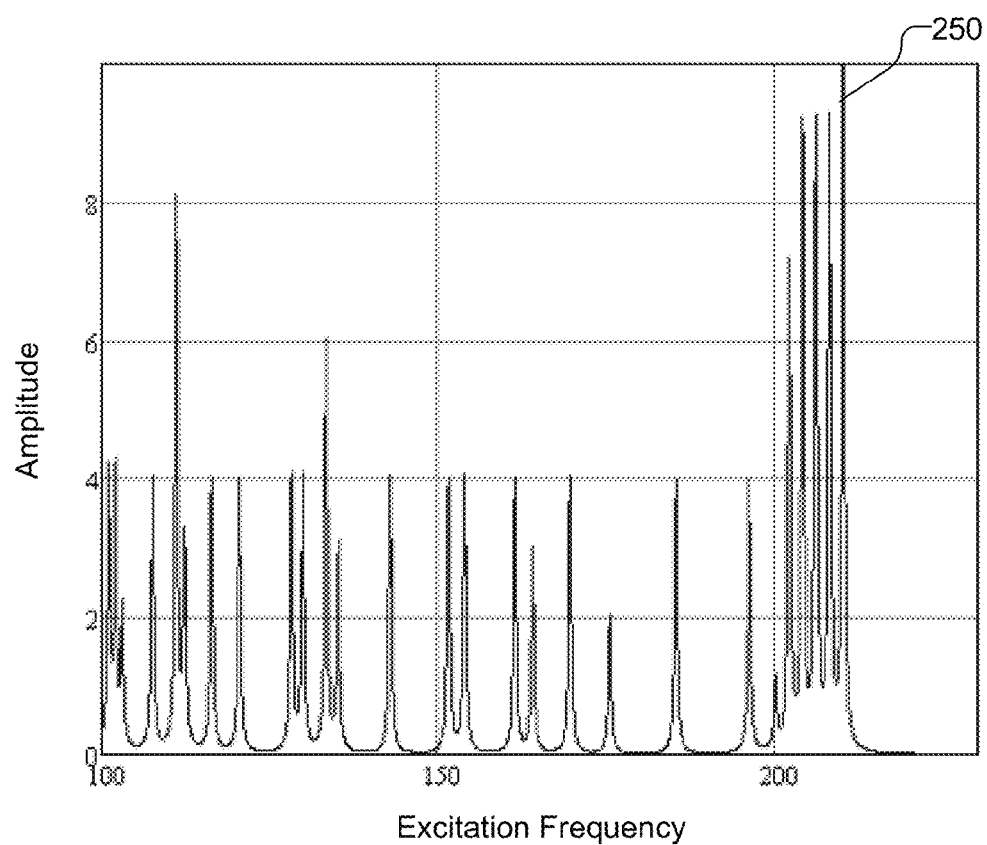
FIG. 24 illustrates an ESR spectrum with the amplitude of the integrated photoluminescence emitted from the matrix of nitrogen vacancy centers for the write field distribution of FIGS. 21A and 21B with respect to various excitation frequencies.
Figure 25:
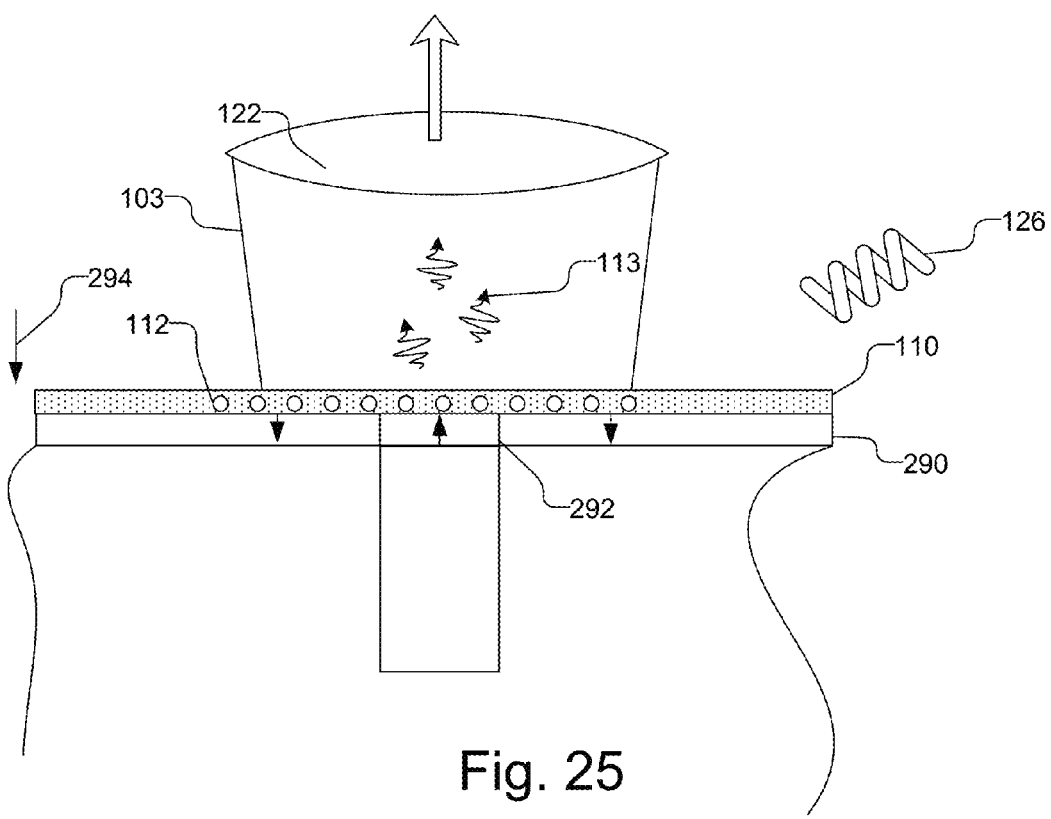
FIG. 25 schematically illustrates a diamond film with a plurality of nitrogen vacancy centers that is positioned to measure a write field footprint from a recording head.

In general, however, the write field profile produced by recording heads is neither homogenous nor radially symmetric. FIG. 20, by way of example, illustrates a plan view of the a portion of an ABS of a recording head showing a write pole 232 with a wrap-around shield 234 and a write gap 236 there between. FIG. 21A illustrates a write field profile of a recording head of FIG. 20 in the down track direction, where a maximum write field is present at the write gap 236 and the leading edge of the write pole 232 has a smaller write field. FIG. 21B illustrates a write field profile of the recording head of FIG. 20 in the cross track direction, where only half of the write field distribution is shown starting at the track center. FIG. 22 illustrates a matrix of evenly spaced NV centers 112 in a diamond film 110, similar to that shown in FIG. 12, but with the spatial extent of different values of the write field from FIGS. 21A and 21B illustrated as semi-circles. It should be noted that for simplification the semi-circles represent the field distributions from FIGS. 21A and 21B in an idealized form. FIGS. 23A, 23B, and 23C illustrate NV centers from the matrix of NV centers illustrated in FIG. 22 that contribute to the ODMR measurement at different write field values, similar to that shown in FIGS. 14A, 14B, and 14C. FIG. 24 is an ESR frequency spectrum illustrating the amplitude of the integrated PL from the NV centers at various excitation frequencies. As discussed previously, the spectral line 250 at the highest excitation frequency represents the write field at the write gap 236. Characteristics of the recording head may be determined using the spectral lines, such as the surface area of the write pole based on the total number of contributing NVs determined from lines 200 to 250, and a width near the write gap of the write head. Additionally, the magnetic write-width may be determined, e.g., from the amplitude of spectral line 250, which is proportional to the number of contributing NV centers. The magnitude of the write field at the write gap may be determined from the resonance frequency represented by spectral line 250 using equation 1. The number of spaces between the number of NV centers (#NV-1) may be multiplied by the known spacing between the NV centers to determine the magnetic write-width. It should be noted that for simplification the semi-circles represent the field distribution shown in FIGS. 21A and 21B in an idealized form. The peak write-field may be determined based on the magnitude of the write field associated with the excitation frequency at spectral line 250 based on equation 1. The shape and surface area could also be determined by fitting a magnetic model of the write-pole to the ODMR spectrum A write foot-print measurement may be performed using a quasi-static technique that closely emulates the writing process. FIG. 25, for example, schematically illustrates the measurement of ODMR from a diamond film 110 with a matrix of evenly distributed NV centers 112, similar to FIG. 22, with a magnetic recording medium 290 deposited on the diamond film 110. The write foot-print of the recording head 112 may be determined by applying a bias field 294 and writing a reversal domain 292 on the recording medium 290 and the stray field is measured by evaluating the resonance spectrum of the integral PL intensity in the same way as described for the write-field, discussed above. The write foot-print may be measured for conventional recording heads as well as energy assisted magnetic recording (HAMR, MAMR). Because the stray-field from the reversal domain is essentially homogeneous, the amplitude of the ESR and therefore the number of contributing NV centers translates directly to the area of the reversal domain and consequently the effective magnetic write-width.

Figure 26:
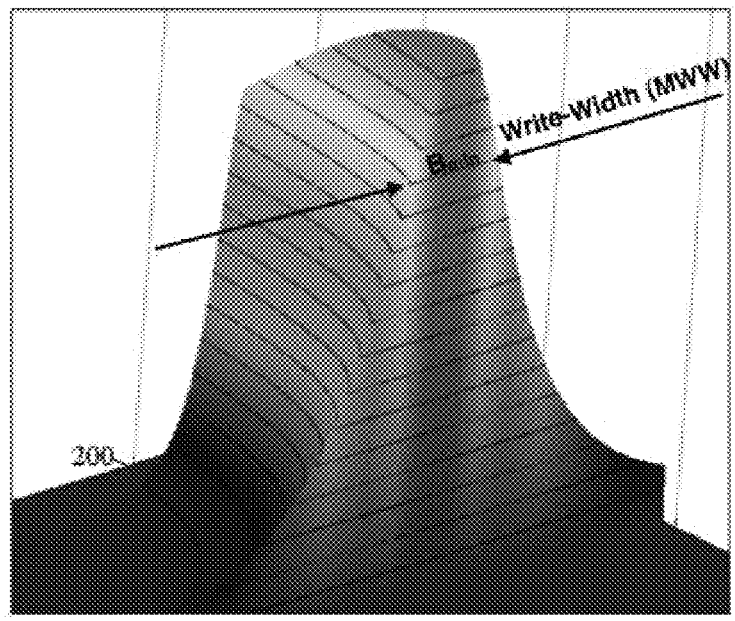
FIG. 26 illustrates a three-dimensional model of a write field distribution from a write head and illustrates the effective magnetic write-width.
Figure 27:
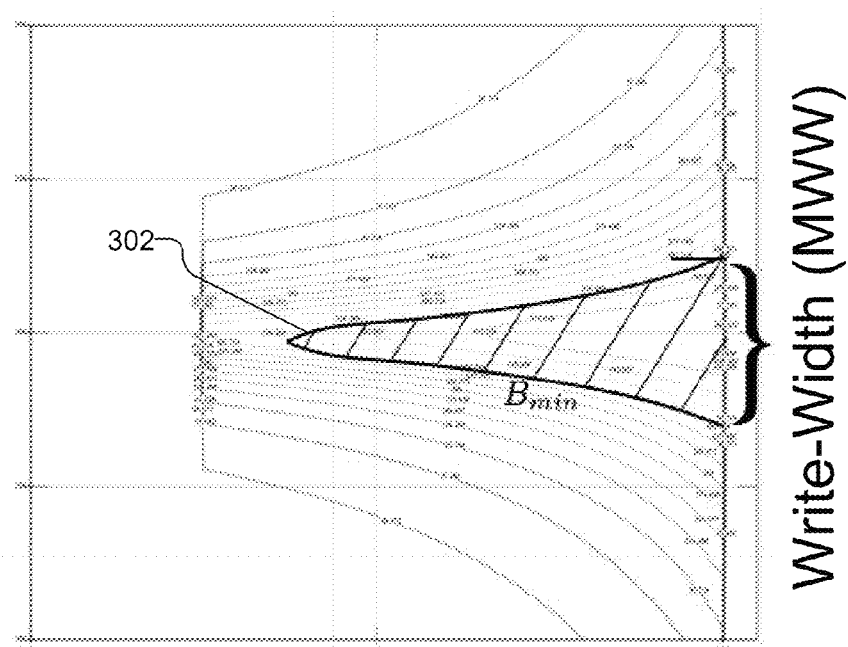
FIG. 27 illustrates the write field contours of the write field distribution from FIG. 26.

Additionally, the effective magnetic write-width (MWW) may be determined from the ODMR spectrum using NV centers without a requirement of a strict equidistance distribution of the NV centers in a matrix. For example, a known average density of the NV centers may be used to determine the magnetic write width. FIG. 26, by way of example, illustrates a three-dimensional model of a write field distribution from a write head for perpendicular recording that is based on an assumed two-dimensional write field distribution that is an approximation of the write field distributions illustrated in FIGS. 21A and 21B. As illustrated in FIG. 26, the effective magnetic write-width is defined at the minimum write field (Bmin), which is the write field that is sufficiently high to write on the recording medium, as determined by the coercivity of the recording medium. FIG. 27 illustrates the write field contours of the write field distribution from FIG. 26. The minimum write field Bmin is identified in FIG. 27 as the dark contour line 302 defining the shaded area, where the shaded area includes write field values greater than the minimum write field Bmin. The maximum write field Bmax is at the right edge, e.g., the write gap, at the center of the pole.

Figure 28:
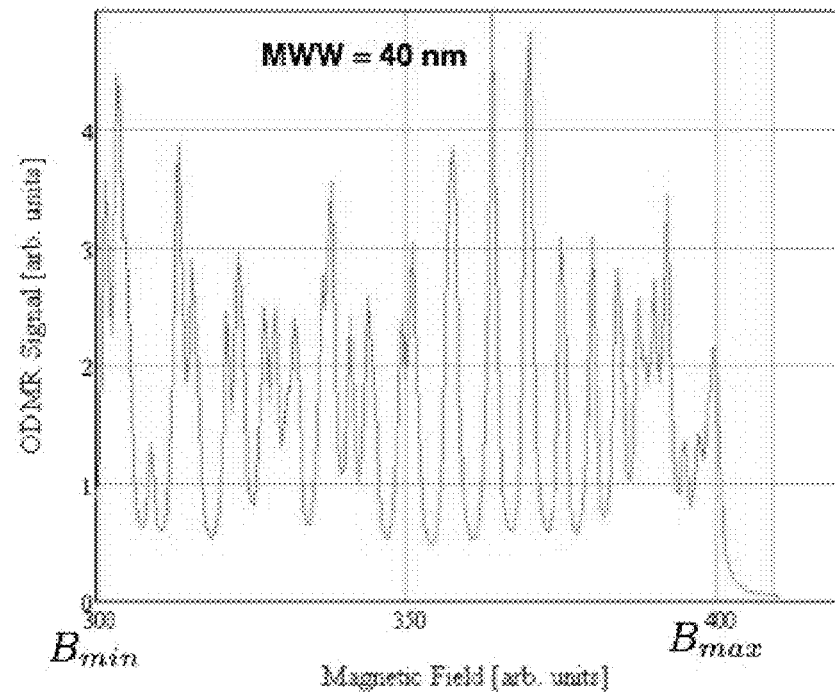
FIG. 28 illustrates a measured ODMR spectrum, e.g., the ODMR signal between the minimum write field (Bmin) to the maximum write field (Bmax), produced by write fields in the area enclosed by the black contour line in FIG. 27.
Figure 29:
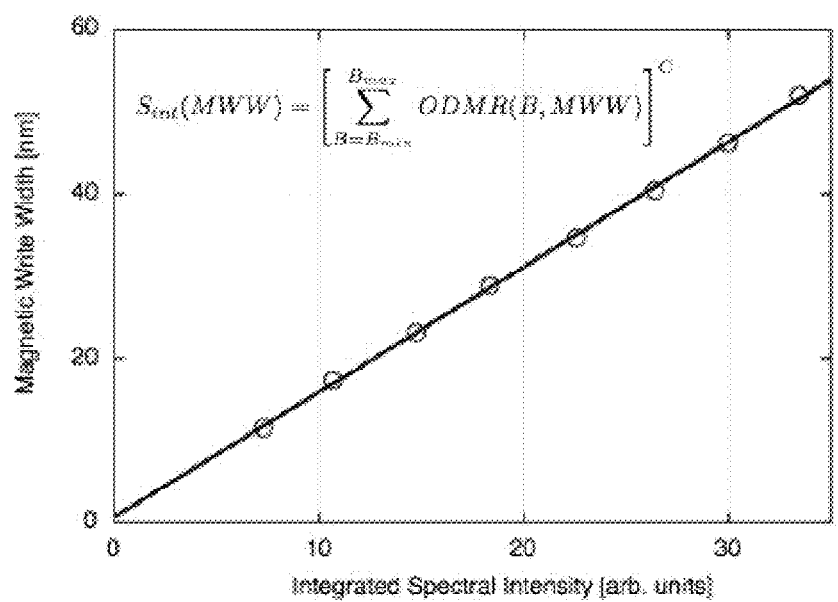
FIG. 29 is a graph illustrating linear dependence of the integrated spectral intensity $S_{int}$ on the magnetic write width.

FIG. 28 illustrates a measured ODMR spectrum, e.g., the ODMR signal between the minimum write field Bmin to the maximum write field Bmax, which is produced by write fields in the area enclosed by the black contour line 302 in FIG. 27. The ODMR spectrum may be integrated over a range Bmin to Bmax to generate an intensity value $S_{int}$ as follows.

$$S_{int}(MWW) = \left[\sum_{B=Bmin}^{Bmax} ODMR(B, MWW)\right]^C. \qquad \text{eq. 4}$$

Where C is a constant that may be determined through calibration. As illustrated in FIG. 29, the integrated spectral intensity $S_{int}$ has a linear dependence on the magnetic write width, when a small exponential constant C is used. The constant C may remain the same if the minimum write field Bmin is varied, e.g., by changing the write current, and depends on the density of the NV centers, where for an equidistant distribution of NV centers, $C=2/\pi$. The density value assumes a distribution of distances with an average distance value that has some standard deviation. Thus, to determine the effective magnetic write width, the ODMR spectrum may be measured and the integrated spectral intensity $S_{int}$ calculated using equation 4, which is correlated to the magnetic write width as illustrated in FIG. 29. Because the location of the Bmin contour line and Bmax also depend on the write-current, the magnetic write width can be measured as a function of the bias level.

Figure 30A:
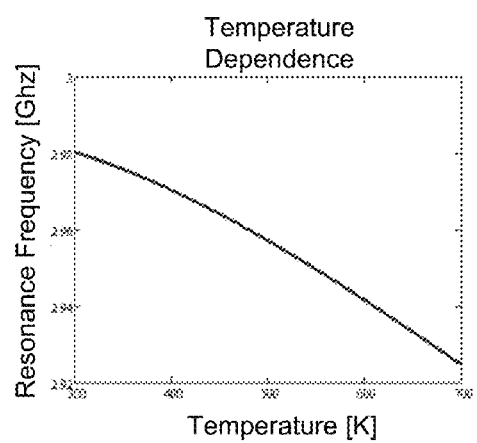
FIGS. 30A and 30B illustrate the temperature dependence of the ESR frequency and resulting resonance lines at different temperatures, e.g., 300° K and 700° K.
Figure 30B:
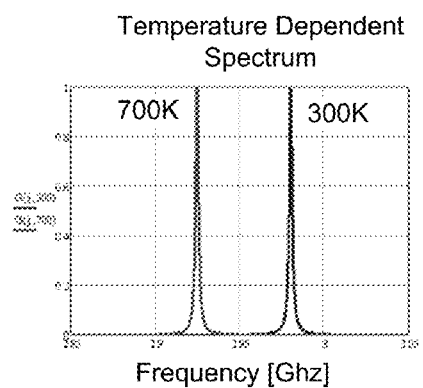

In addition to measuring characteristics such as physical dimensions of the write pole 116 and the strength of the magnetic field B, the NV centers 112 in a diamond film may be used to measure the heat produced by a bias controlled thermal device. In one embodiment, for example, the near-field power at an aperture of a write head for Heat-Assisted Magnetic Recording (HAMR) may be tested, but it should be understood that characteristics of any device that produces heat using a bias controlled thermal device may be measured. Characteristics related to the thermal device that may be determined include, e.g., power, temperature with respect to bias signal, spatial extent of the thermal device or near-field aperture, and heating characteristics such as the spatial extent of heating and the heating width produced by the device. These characteristics may be determined in the same manner as the write pole related characteristics discussed above, where heat as opposed to a magnetic field is used. As illustrated in FIG. 2, the axial zero field splitting parameter D(T) of an NV center is temperature dependent. With increasing temperature the energy gap between the $m_S=0$ and $m_S=-1, +1$ spin states is reduced and consequently the ESR frequency is shifted to lower values. FIG. 30A, by way of example, illustrates the temperature dependence of the ESR frequency with respect to temperature and FIG. 30B illustrates resulting resonance lines at different temperatures, e.g., 300° K and 700° K. Thus, by employing ODMR, the NV center may be used to measure local temperatures on the recording head with high spatial resolution, and thus, is suitable to characterize, e.g., near-field power at an aperture of a HAMR write head.

Figure 31:
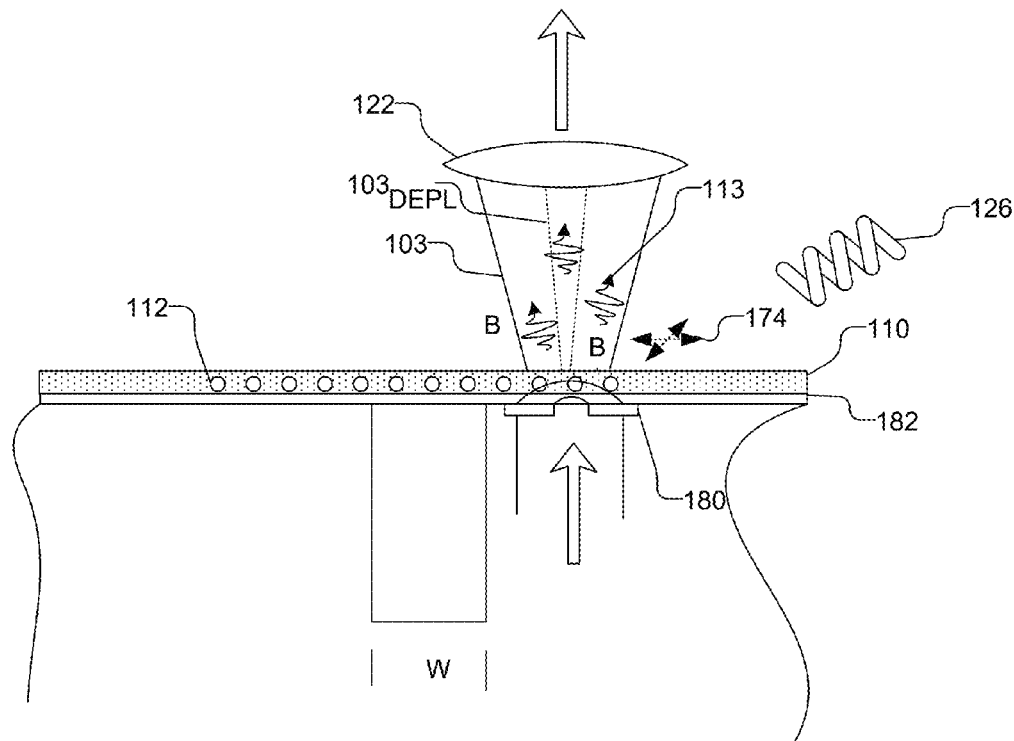
FIG. 31 schematically illustrates a diamond film with a plurality of nitrogen vacancy centers that is positioned to measure a near field aperture 180 of a Heat Assisted Magnetic Recording write head.

FIG. 31, by way of example, schematically illustrates the measurement of ODMR from a diamond film 110 with NV centers 112, similar to FIG. 9, with the diamond film 110 in contact with ABS of the recording head 114 having a near field aperture 180, e.g., used with a HAMR write head. In heat assisted magnetic recording (HAMR), the recording medium is locally heated by a near-field emanating from a nano-aperture with, e.g. d=30 nm opening. The recording head that uses HAMR includes both a write pole and a thermal device, e.g., laser light source, that heats the recording medium through the near-field aperture 180. As discussed above in reference to FIG. 1, the thermal device of the recording head 114 instead of or in addition to the write pole may be controlled via the probe card 132 and the biasing source 131. The biasing source 131 used to control the thermal device may be, e.g., pulsed or DC and may be a constant or varying magnitude. If desired, separate probe cards and/or biasing sources may be used to control the write pole and thermal device. For example, multiple probes from a single probe card 132 may be connected to multiple biasing sources in order to separately engage either the write or the HAMR thermal device, or both, in situ, and either in sequential or simultaneous operation.

Figure 32:
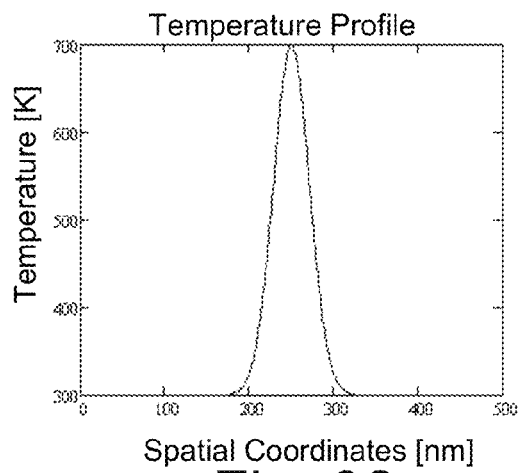
FIG. 32 illustrates the temperature profile produced by a near field aperture used in a Heat Assisted Magnetic Recording write head.

FIG. 32 illustrates the temperature profile produced by a near field aperture used in a HAMR write head. The NV centers 112 in the diamond film 110 may be used to measure the power of the near field at the aperture and/or the spatial extent of the aperture 180 in the same manner as the magnetic field and/or spatial extent of the write pole is measured. The diamond film 110 may be coated with a thin heat absorption layer 182, e.g., a few nanometers thick, that has low thermal conductivity, e.g. $SiO_2$, that functions as the recording medium to be heated. The diamond film 110 may be held close to or in contact with the ABS of the recording head 114. Moreover, the diamond film 110 may be deposited on the ABS of the recording head 114. Further, if desired, the diamond film 110 may be on the tip of an AFM arm as discussed above. The diamond film 110 may be, e.g., implanted with the NV centers 112 or may be a film that is embedded with nano-diamonds having NV centers. The diamond film 110 may be a mono crystalline diamond film with a matrix of equally spaced NV centers to measure the spatial extent of the near field aperture 180 and its power. The diamond film 110 may be a mono crystalline diamond film with a random distribution of NV centers 112 to measure the heating power with an estimate of the spatial extent of the near field aperture 180. If the diamond film 110 is a film with suspended nano-diamonds having a random distribution, the heating power of the near field aperture 180 may be measured.

As illustrated in FIG. 31, the recording head 114, including the nano-aperture 180, is brought into contact with or sufficiently near the heat absorption layer 182 on the diamond film 110 that the near-field emanating from the aperture 180 locally increases the temperature of the heat absorption layer 182. The increase in temperature ΔT affects the electronic state of the NV centers 112 in the diamond film 110. An example of a temperature profile across the aperture is depicted in FIG. 32. As can be seen, the maximum heating occurs in the center of the spatial extent of the near-field aperture.

Figure 34:
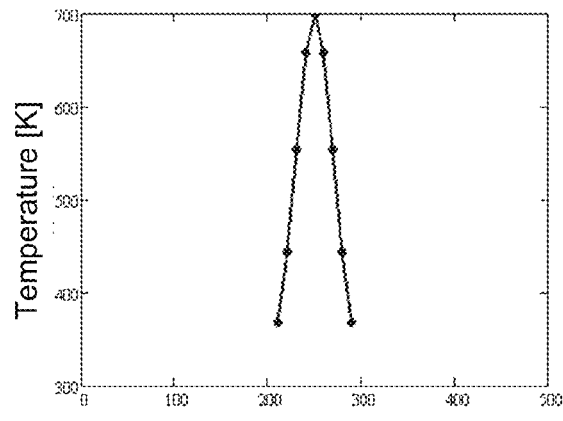
FIG. 34 illustrates a temperature profile extracted from an ESR spectrum.

As discussed above, a light source 102 (shown in FIG. 1) produces excitation illumination 103 that is incident on the diamond film 110 while in an external RF excitation field with varying excitation frequencies or pulse sequence produced by the RF antenna 126. In response to the excitation illumination 103 and while the near-field is produced by aperture 180, the NV center produces spin dependent PL 113 that is collected by the objective lens 122 and provided to the detector 130 (shown in FIG. 1). If desired, depletion illumination $103_{DEPL}$ may be scanned with respect to the recording head in two dimensions to measure ODMR. The integral PL emitted by the NVs is collected with a high numerical aperture objective lens 122 while applying an RF-field of varying frequency or a pulse sequence. A magnetic field may be produced by the write pole or an external magnetic field source, or no magnetic field may be used. Using a matrix of equally spaced NV centers, a frequency spectrum of the ODMR signal, such as that illustrated in FIG. 33, may be generated and may be evaluated to extract temperature information, as illustrated in FIG. 34 in the same way as described for the write-field measurement, and using the known Temperature/ESR dependence, e.g., illustrated in FIGS. 30A and 30B. As can be seen in FIGS. 30A and 30B, temperature is inversely related to the ESR frequency, and thus, the minimum excitation frequency in the ESR spectrum is used to determine the maximum temperature. Additionally, because the maximum heating occurs at the center of the near-field aperture, the number of spectral lines in the ESR spectrum that are associated with the center of the near-field aperture may be used to determine the spatial extent of the near-field aperture. Moreover, if desired, the heat produced by the thermal device may be varied, e.g., by varying the applied bias signal to the thermal device, while producing a constant excitation frequency from the RF antenna 126. For example, the excitation frequency of the RF antenna 126 may be set at a level at which a known good thermal device in a recording head heats an absorption layer 182 to a specific temperature, and sample recording heads may be tested at that excitation frequency to determine the bias signal necessary to produce same temperature. Thus, the efficiency of the thermal device in the recording head may be determined.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method comprising:
   providing a bias signal to a recording head that includes a write pole to produce a magnetic field from the recording head, wherein a crystal film with nitrogen vacancy centers is positioned in the magnetic field;
   providing an excitation field to the crystal film;
   producing excitation illumination that is incident on the crystal film;
   measuring Optically Detected Spin Resonance (ODMR) by detecting a decrease in a spin dependent photoluminescence in response to the magnetic field, the excitation field and the excitation illumination caused by electron spin resonance (ESR) of the nitrogen vacancy centers; and
   determining a characteristic of the recording head using the ODMR.

2. The method of claim 1, wherein the ODMR is measured at varying excitation frequencies of the excitation field.

3. The method of claim 1, wherein the characteristic of the recording head is efficiency of the recording head as a function of bias signal level.

4. The method of claim 1, wherein the crystal film is attached to an air bearing surface of the recording head.

5. The method of claim 1, wherein the recording head further comprises a thermal device and a near-field aperture, the method further comprising:
   providing a second bias signal to the thermal device to heat the crystal film using the near-field aperture; and
   determining a second characteristic of the recording head using measured ODMR based on heating of the crystal film by the thermal device and the near-field aperture.

6. The method of claim 5, wherein the second characteristic of the recording head is a near-field power of the near-field aperture.

7. The method of claim 5, wherein the second characteristic of the recording head is a spatial extent of the near-field aperture.

8. The method of claim 5, further comprising providing a plurality of bias signals with different levels to the thermal device and wherein the second characteristic of the recording head is a function of the heat produced at different levels of bias signals.

9. The method of claim 5, wherein the bias signal provided to the recording head and the second bias signal provided to the thermal device are provided sequentially or serially.

10. An apparatus comprising:
    a biasing source configured to provide a bias signal;
    a probe card coupled to the biasing source and configured to be connected to a recording head that includes a write pole to provide the bias signal to the recording head that causes the recording head to produce a magnetic field;
    a light source that produces excitation illumination that is incident on a crystal film with nitrogen vacancy centers that is in the magnetic field produced by the recording head;
    a radio frequency antenna that provides an excitation field to the crystal film;
    a microscope configured to detect photoluminescence produced by the nitrogen vacancies in response to the excitation illumination; and
    a processor coupled to the microscope and configured to measure Optically Detected Spin Resonance (ODMR) by detecting a decrease in a spin dependent photoluminescence in response to the magnetic field, the excitation field, and the excitation illumination caused by electron spin resonance (ESR) of the nitrogen vacancy centers, and determine a characteristic of the recording head using the ODMR.

11. The apparatus of claim 10, wherein the ODMR is measured at varying excitation frequencies of the excitation field.

12. The apparatus of claim 10, wherein the characteristic of the recording head is efficiency of the recording head as a function of bias signal level.

13. The apparatus of claim 10, wherein the crystal film is attached to an air bearing surface of the recording head.

14. The apparatus of claim 10, wherein the recording head further comprises a thermal device and a near-field aperture, the apparatus further comprising:

a second biasing source configured to provide a second bias signal to the thermal device to heat the crystal film using the near-field aperture;

wherein the processor is further configured to determine a second characteristic of the recording head using measured ODMR based on heating of the crystal film by the thermal device and the near-field aperture.

15. The apparatus of claim 14, wherein the second characteristic of the recording head is a near-field power of the near-field aperture.

16. The apparatus of claim 14, wherein the second characteristic of the recording head is a spatial extent of the near-field aperture.

17. The apparatus of claim 14, wherein the second biasing source provides a plurality of bias signals with different levels to the thermal device and wherein the second characteristic of the recording head is a function of the heat produced at different levels of bias signals.

18. The apparatus of claim 14, wherein the bias signal provided to the recording head and the second bias signal provided to the thermal device are provided sequentially or serially.

19. A method comprising:
providing a bias signal to a device that includes a thermal device that is controlled by the bias signal to produce heat, wherein a crystal film with nitrogen vacancy centers is positioned to be heated by the thermal device;
providing an excitation field to the crystal film;
producing excitation illumination that is incident on the crystal film;
measuring Optically Detected Spin Resonance (ODMR) by detecting a decrease in a spin dependent photoluminescence in response to the heat, the excitation field and the excitation illumination caused by electron spin resonance (ESR) of the nitrogen vacancy centers; and
determining a characteristic of the device using the ODMR.

20. The method of claim 19, wherein a heat absorption layer is disposed between the thermal device and the crystal film.

21. The method of claim 19, wherein the ODMR is measured at varying excitation frequencies of the excitation field.

22. The method of claim 19, further comprising providing a plurality of bias signals with different levels to the device and wherein the characteristic of the device is a function of the heat produced at different levels of bias signals.

23. The method of claim 19, wherein the device is a recording head that includes the thermal device and a near-field aperture.

24. The method of claim 23, wherein the characteristic of the device is a near-field power of the near-field aperture.

25. The method of claim 23, wherein the nitrogen vacancy centers have a known density and wherein determining the characteristic of the head uses the known density of the nitrogen vacancy centers.

26. The method of claim 25, wherein the characteristic of the device comprises a spatial extent of the near-field aperture.

27. The method of claim 26, wherein the spatial extent of the near-field aperture is determined based on a spatial extent of the heat produced by the recording head.

28. The method of claim 26, further comprising:
determining a number of nitrogen vacancy centers contributing to an ODMR signal measured at one or more excitation frequencies based on a contrast of the ODMR signal at the one or more excitation frequencies and a known contrast of the ODMR signal for a single nitrogen vacancy center;
wherein the spatial extent of the near-field aperture is determined based on the number of nitrogen vacancy centers contributing to the ODMR signal emitting at the one or more excitation frequencies and the known density of the nitrogen vacancy centers.

29. The method of claim 26, further comprising determining a width of the near-field aperture based on the spatial extent of the near-field aperture.

30. The method of claim 26, wherein the ODMR is measured at varying excitation frequencies of the excitation field to produce an ESR spectrum, the method further comprising:
determining a minimum excitation frequency in the ESR spectrum at which an ODMR signal is produced by one or more nitrogen vacancy centers;
determining a number of spectral lines in the ESR spectrum associated with a center of the near-field aperture; and
using the minimum excitation frequency, the number of spectral lines, and the known density of the nitrogen vacancy centers which determines the spatial relation of the spectral lines to determine the spatial extent of the near-field aperture.

31. The method of claim 25, wherein the characteristic of the recording head is a heating width, the method further comprising:
determining a minimum excitation frequency at which an ODMR signal is produced by one or more nitrogen vacancy centers;
determining a number of nitrogen vacancy centers contributing to the ODMR signal at the minimum excitation frequency; and
determining the heating width using the number of nitrogen vacancy centers contributing to the ODMR signal at the minimum excitation frequency and the known density of the nitrogen vacancy centers.

32. The method of claim 31, further comprising determining the heating width as a function of bias level.

33. The method of claim 25, wherein the characteristic of the recording head is a heating width, the method further comprising:
determining an integrated spectral intensity using the ODMR from a minimum heating to a maximum heating and an exponential constant based on the density of the nitrogen vacancy centers; and
determining the heating width based on the integrated spectral intensity.

34. The method of claim 33, further comprising determining the heating width as a function of bias level.

35. The method of claim 25, further comprising:
determining a minimum excitation frequency at which an ODMR signal is produced by one or more nitrogen vacancy centers; and
using the minimum excitation frequency to determine a maximum heating produced by the thermal device.

36. The method of claim 23, wherein adjacent nitrogen vacancy centers are separated by a distance greater than a width of the near-field aperture, further comprising producing relative movement between the recording head and the crystal film thereby scanning a nitrogen vacancy center over the recording head in two dimensions.

37. The method of claim 36, wherein the nitrogen vacancy center is scanned over the near-field aperture and wherein the determined characteristic of the recording head is heating values.

38. The method of claim 36, wherein the nitrogen vacancy center is scanned over the near-field aperture and wherein the determined characteristic of the recording head is a surface area of the near-field aperture.

39. The method of claim 23, wherein adjacent nitrogen vacancy centers are separated by a distance less than a width of the near-field aperture, further comprising:
producing a depletion illumination that is coincident on the crystal film with the excitation illumination;
scanning the coincident excitation illumination and the depletion illumination in two dimensions over the crystal film over a portion of the recording head;
wherein measuring ODMR uses the coincident excitation illumination and depletion illumination.

40. The method of claim 39, wherein the depletion illumination is one of a group consisting essentially of: Stimulated Emission Depletion (STED) illumination and Ground State Depletion (GSD) illumination.

41. The method of claim 39, wherein the excitation illumination and the depletion illumination are scanned over the near-field aperture and wherein the determined characteristic of the recording head is heating values.

42. The method of claim 39, wherein the excitation illumination and the depletion illumination are scanned over the near-field aperture and wherein the determined characteristic of the recording head is a surface area of the near-field aperture.

43. The method of claim 39, wherein the crystal film is attached to an air bearing surface of the recording head.

44. An apparatus comprising:
a biasing source configured to provide bias signals;
a probe card coupled to the biasing source and configured to be connected to a device that includes a thermal device, the probe card provides a bias signal to the device that causes the thermal device to heat a crystal film, the crystal film includes nitrogen vacancy centers;
a light source that produces excitation illumination that is incident on the crystal film;
a radio frequency antenna that provides an excitation field to the crystal film;
a microscope configured to detect photoluminescence produced by the nitrogen vacancies in response to the excitation illumination; and
a processor coupled to the microscope and configured to measure Optically Detected Spin Resonance (ODMR) by detecting a decrease in a spin dependent photoluminescence in response to the heat, the excitation field, and the excitation illumination caused by electron spin resonance (ESR) of the nitrogen vacancy centers; and determine a characteristic of the device using the ODMR.

45. The apparatus of claim 44, wherein a heat absorption layer is disposed between the thermal device and the crystal film.

46. The apparatus of claim 44, wherein the ODMR is measured at varying excitation frequencies of the excitation field.

47. The apparatus of claim 44, wherein the biasing source is configured to provide a plurality of bias signals with different levels to the device and wherein the characteristic of the device is a function of the heat produced at different levels of bias signals.

48. The apparatus of claim 44, wherein the device is a recording head that includes the thermal device and a near-field aperture.

49. The apparatus of claim 48, wherein the characteristic of the device is a near-field power of the near-field aperture.

50. The apparatus of claim 48, wherein the nitrogen vacancy centers have a known density and wherein the processor is configured to determine the characteristic of the head using the known density of the nitrogen vacancy centers.

51. The apparatus of claim 50, wherein the characteristic of the device comprises a spatial extent of the near-field aperture.

52. The apparatus of claim 51, wherein the processor is configured to determine the spatial extent of the near-field aperture based on a spatial extent of the heat produced by the recording head.

53. The apparatus of claim 51, wherein the processor is configured to:
determine a number of nitrogen vacancy centers contributing to an ODMR signal measured at one or more excitation frequencies based on a contrast of the ODMR signal at the one or more excitation frequencies and a known contrast of the ODMR signal for a single nitrogen vacancy center;
wherein the spatial extent of the near-field aperture is determined based on the number of nitrogen vacancy centers contributing to the ODMR signal emitting at the one or more excitation frequencies and the known density of the nitrogen vacancy centers.

54. The apparatus of claim 51, wherein the processor is further configured to determine a width of the near-field aperture based on the spatial extent of the near-field aperture.

55. The apparatus of claim 51, wherein the processor is configured to measure ODMR at varying excitation frequencies to produce an ESR spectrum, the processor is further configured to:
determine a minimum excitation frequency in the ESR spectrum at which an ODMR signal is produced by one or more nitrogen vacancy centers;
determine a number of spectral lines in the ESR spectrum associated with a center of the near-field aperture; and
use the minimum excitation frequency, the number of spectral lines, and the known density of the nitrogen vacancy centers which determines the spatial relation of the spectral lines to determine the spatial extent of the near-field aperture.

56. The apparatus of claim 50, wherein the characteristic of the recording head is a heating width, and wherein the processor is further configured to:
determine a minimum excitation frequency at which an ODMR signal is produced by one or more nitrogen vacancy centers;
determine a number of nitrogen vacancy centers contributing to the ODMR signal at the minimum excitation frequency; and
determine the heating width using the number of nitrogen vacancy centers contributing to the ODMR signal at the minimum excitation frequency and the known density of the nitrogen vacancy centers.

57. The apparatus of claim 56, wherein the heating width is determined as a function of bias level.

58. The apparatus of claim 50, wherein the characteristic of the recording head is a heating width, and wherein the processor is configured to:

determine an integrated spectral intensity using the ODMR from a minimum heating to a maximum heating and an exponential constant based on the density of the nitrogen vacancy centers; and determine the heating width based on the integrated spectral intensity.

59. The apparatus of claim 58, wherein the heating width is determined as a function of bias level.

60. The apparatus of claim 50, wherein the processor is further configured to:

determine a minimum excitation frequency at which an ODMR signal is produced by one or more nitrogen vacancy centers; and use the minimum excitation frequency to determine a maximum heating produced by the thermal device.

61. The apparatus of claim 48, wherein adjacent nitrogen vacancy centers are separated by a distance greater than a width of the near-field aperture, the apparatus further comprising at least one actuator to produce relative movement between the recording head and the crystal film thereby scanning a nitrogen vacancy center over the recording head in two dimensions.

62. The apparatus of claim 61, wherein the nitrogen vacancy center is scanned over the near-field aperture and wherein the determined characteristic of the recording head is heating values.

63. The apparatus of claim 61, wherein the nitrogen vacancy center is scanned over the near-field aperture and wherein the determined characteristic of the recording head is a surface area of the near-field aperture.

64. The apparatus of claim 48, wherein adjacent nitrogen vacancy centers are separated by a distance less than a width of the near-field aperture, the apparatus further comprising:

a second light source that produces depletion illumination that is coincident on the crystal film with the excitation illumination;

at least one mirror to scan the coincident excitation illumination and the depletion illumination in two dimensions over the crystal film over a portion of the recording head;

wherein the processor is configured to use the coincident excitation illumination and depletion illumination to measure the ODMR.

65. The apparatus of claim 64, wherein the depletion illumination is one of a group consisting essentially of: Stimulated Emission Depletion (STED) illumination and Ground State Depletion (GSD) illumination.

66. The apparatus of claim 64, wherein the excitation illumination and the depletion illumination are scanned over the near-field aperture and wherein the determined characteristic of the recording head is heating values.

67. The apparatus of claim 64, wherein the excitation illumination and the depletion illumination are scanned over the near-field aperture and wherein the determined characteristic of the recording head is a surface area of the near-field aperture.

68. The apparatus of claim 64, wherein the crystal film is attached to an air bearing surface of the recording head.

69. A method comprising:

providing a bias signal to a recording head that includes a write pole to produce a magnetic field from the recording head;

scanning a probe having a probe tip comprising a crystal particle with at least one nitrogen vacancy center through the magnetic field produced by the recording head;

providing an excitation field to the crystal particle;

producing excitation illumination that is incident on the crystal particle;

measuring Optically Detected Spin Resonance (ODMR) by detecting a decrease in a spin dependent photoluminescence in response to the excitation illumination caused by electron spin resonance (ESR) of the at least one nitrogen vacancy center; and determining a characteristic of the recording head using the ODMR.

70. The method of claim 69, wherein the ODMR is measured at varying excitation frequencies of the excitation field.

71. The method of claim 69, further comprising providing a plurality of bias signals with different levels to the recording head.

72. The method of claim 69, wherein the recording head further comprises a thermal device and a near-field aperture, the method further comprising:

providing a second bias signal to the thermal device to heat the crystal film using the near-field aperture; and determining a second characteristic of the recording head using measured ODMR based on heating of the crystal film by the thermal device and the near-field aperture.

73. The method of claim 72, wherein the second characteristic of the recording head is a near-field power of the near-field aperture.

74. The method of claim 72, wherein the second characteristic of the recording head is a spatial extent of the near-field aperture.

75. The method of claim 72, further comprising providing a plurality of bias signals with different levels to the thermal device and wherein the second characteristic of the recording head is a function of the heat produced at different levels of bias signals.

76. The method of claim 72, wherein the bias signal provided to the recording head and the second bias signal provided to the thermal device are provided sequentially or serially.

77. An apparatus comprising:

a biasing source configured to provide a bias signal;

a probe card coupled to the biasing source and configured to be connected to a recording head that includes a write pole to provide the bias signal to the recording head that causes the recording head to produce a magnetic field;

a probe having a probe tip comprising a crystal particle with at least one nitrogen vacancy center, the probe configured to be scanned through the magnetic field produced by the recording head;

a light source that produces excitation illumination that is incident on the crystal particle;

a radio frequency antenna that provides an excitation field to the crystal particle;

a microscope configured to detect photoluminescence produced by the at least one nitrogen vacancy in the crystal particle;

a processor coupled to the microscope and configured to measure Optically Detected Spin Resonance (ODMR) by detecting a decrease in a spin dependent photoluminescence in response to the excitation illumination caused by electron spin resonance (ESR) of the at least one nitrogen vacancy center; and determine a characteristic of the recording head using the ODMR.

78. The apparatus of claim 77, wherein the ODMR is measured at varying excitation frequencies of the excitation field.

79. The apparatus of claim 77, further comprising providing a plurality of bias signals with different levels to the recording head.

80. The apparatus of claim 77, wherein the probe is scanned over a write pole of the recording head and wherein the determined characteristic of the recording head is magnetic field values.

81. The apparatus of claim 77, wherein the recording head further comprises a thermal device and a near-field aperture, the apparatus further comprising:
- a second biasing source configured to provide a second bias signal to the thermal device to heat the crystal film using the near-field aperture;
- wherein the processor is further configured to determine a second characteristic of the recording head using measured ODMR based on heating of the crystal film by the thermal device and the near-field aperture.

82. The apparatus of claim 81, wherein the second characteristic of the recording head is a near-field power of the near-field aperture.

83. The apparatus of claim 81, wherein the second characteristic of the recording head is a spatial extent of the near-field aperture.

84. The apparatus of claim 81, wherein the second biasing source provides a plurality of bias signals with different levels to the thermal device and wherein the second characteristic of the recording head is a function of the heat produced at different levels of bias signals.

85. The apparatus of claim 81, wherein the bias signal provided to the recording head and the second bias signal provided to the thermal device are provided sequentially or serially.

* * * * *